United States Patent
Arai et al.

(10) Patent No.: US 7,402,996 B2
(45) Date of Patent: Jul. 22, 2008

(54) INSTRUMENT AND METHOD FOR MEASURING THREE-DIMENSIONAL MOTION

(75) Inventors: Kenichi Arai, Shiogama (JP); Shin Yabukami, Sendai (JP); Hiroyasu Kanetaka, Sendai (JP)

(73) Assignee: Japan Science and Technology Agency, Saitama (JP)

( * ) Notice: Subject to any disclaimer, the term of this patent is extended or adjusted under 35 U.S.C. 154(b) by 0 days.

(21) Appl. No.: 11/547,050

(22) PCT Filed: Mar. 31, 2005

(86) PCT No.: PCT/JP2005/006275

§ 371 (c)(1),
(2), (4) Date: Jul. 18, 2007

(87) PCT Pub. No.: WO2005/094677

PCT Pub. Date: Oct. 13, 2005

(65) Prior Publication Data

US 2007/0252586 A1    Nov. 1, 2007

(30) Foreign Application Priority Data

Mar. 31, 2004    (JP) .............................. 2004-106789

(51) Int. Cl.
G01B 7/14 (2006.01)
G01B 7/00 (2006.01)
G01R 33/00 (2006.01)

(52) U.S. Cl. .................. 324/207.17; 324/207.11; 324/207.15; 324/207.16; 324/244

(58) Field of Classification Search ............ 324/207.11, 324/207.15, 207.16, 207.17, 207.24, 207.25, 324/244, 260; 73/514.16, 514.31, 514.39; 338/32 R, 32 H
See application file for complete search history.

(56) References Cited

U.S. PATENT DOCUMENTS

| 3,822,694 A | 7/1974 | Mills |
| 4,776,348 A | 10/1988 | Bando et al. |

FOREIGN PATENT DOCUMENTS

| JP | 49-125133 A | 11/1974 |
| JP | 53-103690 A | 9/1978 |
| JP | 62-179432 A | 8/1987 |
| JP | 6-86717 U | 12/1994 |
| JP | 7-323023 A | 12/1995 |
| JP | 2000-193409 A | 7/2000 |
| JP | 2002-355264 A | 12/2002 |
| JP | 2004-229943 A | 8/2004 |
| JP | 2005-91203 A | 4/2005 |

OTHER PUBLICATIONS

S. Yabukami, et al., "Error Analysis of a Jaw-Tracking System Using Two Magnets", 2003, pp. 765-770, vol. 27, No. 6.

*Primary Examiner*—Bot LeDynh
(74) *Attorney, Agent, or Firm*—Sughrue Mion, PLLC

(57) ABSTRACT

An instrument (10) for measuring three-dimensional motion in a living body comprises a plurality of magnetism generators (12$_i$) fixed to one of at least two objects (44, 46) moving relatively in the living body, a plurality of magnetic field sensors (14$_j$) fixed to the other object in order to perform noncontact detection of the magnetic field of each magnetism generator (12$_i$), and a signal processing means (26) for calculating relative position and direction between each magnetism generator (12$_i$) and each magnetic field sensor (14$_j$) according to a magnetic field detected by each magnetic field sensor (14$_j$). The number of magnetism generators (12$_i$) and magnetic field sensors (14$_j$) is at least five, respectively.

14 Claims, 17 Drawing Sheets

US 7,402,996 B2

INSTRUMENT AND METHOD FOR MEASURING THREE-DIMENSIONAL MOTION

This is a 371 national phase application of PCT/JP05/06275 filed 31 Mar. 2005, which claims priority to Japanese Patent Application No. 2004-106789 filed 31 Mar. 2004, the content of which is incorporated herein by reference in its entirety.

TECHNICAL FIELD

The present invention relates to an apparatus for and a method of measuring three-dimensional movement by installing magnetic generators and magnetic field sensors on at least two relatively movable objects (for example, a combination of at least two of a part in a living body, movable in unison with an upper jaw, a part in a living body, movable in unison with a lower jaw, a tongue, and an artificial tooth mounted in an oral cavity) and measuring relative three-dimensional movement of one of the objects with respect to the other object.

BACKGROUND ART

Heretofore, apparatus for measuring three-dimensional movement in a living body have been available in the market. For example, an optical jaw movement measuring apparatus is used to measure relative movement of a lower jaw with respect to an upper jaw, which is constructed integrally with a human head. The optical jaw movement measuring apparatus has a light source device mounted on the head or the upper jaw tooth row of an examinee as a fixed source for measuring the movement of the upper jaw of the examinee, and another light source device mounted on the lower jaw tooth row as a fixed source for measuring the movement of the lower jaw.

However, since the light source devices are mounted respectively on the head or the upper jaw tooth row of the examinee and the lower jaw tooth row, the optical jaw movement measuring apparatus is problematic in that the examinee's freedom is greatly limited in measuring jaw movement. Furthermore, the optical nature of the apparatus makes it impossible to make measurements within a shielded space such as an oral cavity.

Other jaw movement measuring apparatus include magnetic jaw movement measuring apparatus. The magnetic jaw movement measuring apparatus are classified into DC magnetic field measuring apparatus for measuring three-dimensional jaw movement by detecting a DC magnetic field generated by a magnetic generator with a magnetic field sensor, and AC magnetic field measuring apparatus for measuring three-dimensional jaw movement by detecting an AC magnetic field generated by a magnetic generator with a magnetic field sensor. Of these measuring apparatus, the DC magnetic field measuring apparatus may possibly have their measuring accuracy and positional accuracy lowered due to externally applied low-frequency noise such as temporal variation in the geomagnetism, the movement of a magnetic body, etc.

The magnetic field sensor of the AC magnetic field measuring apparatus comprises a triaxial coil. When the magnetic field sensor is inserted into an oral cavity, a magnetic field detected by the magnetic field sensor is transmitted through a cable to a signal processor or the like. Since it is difficult to install the triaxial coil and the cable reliably in the oral cavity, when the examinee makes a jaw movement, the magnetic field sensor tends to fluctuate, thereby increasing the measuring error and reducing the positional accuracy of the magnetic field sensor. It is thus difficult to reproduce the jaw movement accurately. Furthermore, inasmuch as the components mounted in the oral cavity are large, the examinee's freedom is greatly limited in measuring jaw movement.

In view of the foregoing problems, a magnetic jaw movement measuring apparatus 200 shown in FIG. 17 has been proposed (see Patent Document 1). The magnetic jaw movement measuring apparatus 200 includes a spherical shell 202, six circularly wound field coils 204 disposed in the spherical shell 202, an attachment 210 rigidly coupled to the lower jaw 208 of an examinee 206 in the spherical shell 202, and a sensor coil 212 coupled to the attachment 210 and comprising three choke coils.

Of the six field coils 204, every two field coils 204 make up a uniaxial coil. While alternating currents are flowing through the field coils 204, generating a magnetic field, when the examinee 206 moves the lower jaw 208 with respect to the upper jaw 214, the sensor coil 212 on the attachment 210 is tilted, changing the amplitude of an AC signal that is induced in the sensor coil 212. The amplitude is detected to measure the three-dimensional movement of the lower jaw 208.

Patent Document 1: Japanese Laid-Open Patent Publication No. 2000-193409

DISCLOSURE OF THE INVENTION

Problems to be Solved by the Invention

With the conventional jaw movement measuring apparatus 200, however, since the field coils 204 and the sensor coil 212 are disposed outside of the examinee 206, positional displacements of the attachment 210 and the sensor coil 212 with respect to the examinee 206 are liable to greatly lower the measuring accuracy of the sensor coil 212, resulting in a large reduction in the positional accuracy of the lower jaw 208. Accordingly, the jaw movement measuring apparatus 200 fails to reproduce the jaw movement accurately.

Furthermore, as the apparatus itself is large in size because the field coils 204 and the sensor coil 212 are disposed outside of the examinee 206, it is difficult to introduce the apparatus into a dental clinic, for example.

It is an object of the present invention to provide an apparatus for and a method of measuring three-dimensional movement to increase the measuring accuracy and positional accuracy of relative three-dimensional movement of at least two objects.

Means for Solving the Problems

An apparatus for measuring three-dimensional movement according to the present invention has a plurality of magnetic generators mounted on one of at least two relatively movable objects, a plurality of magnetic field sensors mounted on the other object, for detecting magnetic fields of the magnetic generators out of contact therewith, and a signal processing means for calculating relative positions and directions between the magnetic generators and the magnetic field sensors from the magnetic fields detected by the magnetic field sensors, wherein the magnetic generators and the magnetic field sensors are paired in at least five combinations. In this case, the two relatively movable objects, on which the magnetic generators and the magnetic field sensors are mounted, comprise two parts, which move relatively to each other in a living body, for example, a part movable in unison with an upper jaw and a part movable in unison with a lower jaw, of the head of the living body.

The magnetic generators are mounted on one of the objects and the magnetic field sensors on the other object. One of the magnetic generators generates a measuring magnetic field, and one of the magnetic field sensors detects the measuring magnetic field. When the measuring magnetic field is generated, an electromagnetic coupling occurs between the one of the magnetic generators and the one of the magnetic field sensors, and the one of the magnetic field sensors converts the measuring magnetic field into an electric signal (voltage) by way of electromagnetic induction.

If there are at least six electromagnetic coupling combinations between the magnetic generators and the magnetic field sensors, then parameters of six-degree-of-freedom movement with respect to the magnetic generators can be determined from the six detected measuring magnetic fields or electric signals, and the relative movement between the two objects can be calculated from the parameters.

With the apparatus for measuring three-dimensional movement according to the present invention, therefore, the relative movement between the two objects can be measured by providing six or more electromagnetic coupling combinations irrespectively of the mounted positions and mounted directions of the magnetic generators and the magnetic field sensors. Therefore, the positional accuracy of the magnetic generators and the magnetic field sensors and the measuring accuracy of the magnetic field sensors are not lowered by the mounted positions and mounted directions of the magnetic generators and the magnetic field sensors.

In order to realize the six or more electromagnetic coupling combinations described above, if there are at least two magnetic generators, then at least three magnetic field sensors should preferably be provided. If there are at least three magnetic generators, then at least two magnetic field sensors should preferably be provided.

Since magnetic generators are mounted on one of the objects and the magnetic field sensors on the other object, the distance between the magnetic generators and the magnetic field sensors is smaller than with the conventional magnetic jaw movement measuring apparatus, and the positional gradient of the magnetic field detected by each of the magnetic field sensors is greater. Therefore, the level of the electric signal output from each of the magnetic field sensors is higher, and the measuring accuracy of each of the magnetic field sensors is higher.

Inasmuch as the magnetic generators and the magnetic field sensors are mounted directly on the two objects, when the two objects move relatively to each other, the magnetic generators and the magnetic field sensors also move in unison with the two objects, respectively.

Therefore, when the two objects move relatively to each other, the magnetic generators and the magnetic field sensors are not positionally shifted from their original positions. Consequently, the measuring accuracy of the magnetic field sensors and the positional accuracy of the magnetic generators and the magnetic field sensors can be increased.

Inasmuch as the magnetic generators and the magnetic field sensors are disposed directly on the two objects, it is easy to reduce the size of the apparatus for measuring three-dimensional jaw movement.

If the total number of combinations of pairs of the magnetic generators and the magnetic field sensors is increased to six or more, then the positional accuracy of the magnetic generators and the magnetic field sensors can further be increased.

Preferably, each of the magnetic generators and the magnetic field sensors is of a planar type, each of the magnetic generators generates a uniaxial magnetic field, and each of the magnetic field sensors detects the uniaxial magnetic field.

Preferably, each of the magnetic generators and the magnetic field sensors comprises a planar coil for generating and detecting the uniaxial magnetic field. The planar coils can easily be mounted on the two objects, and even if the two objects move relatively to each other, any positional shift of the magnetic generators and the magnetic field sensors from their original positions can be further reduced. Since the planar coils can be fabricated by printing or the like, they can be produced more accurately and less costly than biaxial or triaxial coils.

The measuring magnetic field generated by each of the magnetic generators preferably comprises an alternating magnetic field. Since the electric signal output from each of the magnetic field sensors is proportional to the frequency of the alternating magnetic field, each of the magnetic field sensors outputs an electric signal having a higher level as the frequency of the alternating magnetic field is higher. Therefore, the positional resolution of the magnetic generators and the magnetic field sensors with respect to positional detection can be increased.

If the frequency of the alternating magnetic field is increased, then it is possible to eliminate low-frequency noise such as noise due to the commercial frequency, noise due to a changing magnetic field of the geomagnetism, and noise due to moving vehicles. Consequently, the apparatus for measuring three-dimensional movement can be made resistant to low-frequency noise.

Preferably, each of the magnetic generators comprises the planar coil and a capacitor connected in parallel to or in series to the planar coil, and the measuring magnetic field generated by each of the magnetic generators comprises an alternating magnetic field having the resonant frequency of the planar coil and the capacitor.

Reactance components in the magnetic generators can be eliminated by the resonance between the planar coils and the capacitors, thereby making it possible to further increase the level of the electric signal output from each of the magnetic field sensors. Therefore, the positional resolution of the magnetic generators and the magnetic field sensors can be further increased.

In the apparatus for measuring three-dimensional movement, it is necessary to measure initial positions and initial directions of the magnetic generators and the magnetic field sensors that are mounted on the two objects before three-dimensional movement is measured. Therefore, the apparatus for measuring three-dimensional movement preferably further includes a plurality of non-contact calibrating coils, each of the calibrating coils being paired in a total of at least five combinations, wherein calibrating magnetic fields generated by the calibrating coils are detected by the magnetic generators and the magnetic field sensors to measure initial positions and initial directions of the magnetic generators and the magnetic field sensors.

The calibrating coils may be installed directly on either one of the two objects or may be spaced from the two objects. In any case, the calibrating coils should preferably be positioned in the vicinity of the magnetic generators and the magnetic field sensors. If the calibrating coils are installed directly on the two objects, then since the calibrating coils are fixed on the two objects, the positional accuracy of the magnetic generators and the magnetic field sensors can be further increased.

Preferably, each of the calibrating coils comprises a uniaxial, biaxial, or triaxial coil. If each of the calibrating coils comprises a uniaxial coil, then when the calibrating coils are installed directly on the two objects, the calibrating coils are more reliably fixed in place, resulting in a further increase in the positional accuracy of the magnetic generators and the magnetic field sensors. The uniaxial coils can be placed so as not to obstruct natural movement.

The apparatus for measuring three-dimensional movement preferably further includes an electromagnetic coupling switching means for switching electromagnetic coupling combinations between the magnetic generators and the magnetic field sensors and switching electromagnetic coupling combinations between the calibrating coils and the magnetic generators or the magnetic field sensors, and coaxial cables electrically connecting the magnetic generators, the magnetic field sensors, and the calibrating coils to the electromagnetic coupling switching means.

The electromagnetic coupling switching means selects one of the calibrating coils, and selects one of the magnetic generators or one of the magnetic field sensors. Then, a calibrating alternating current power supply supplies a calibrating input signal to the one of the calibrating oils through the electromagnetic coupling switching means. The one of the calibrating coils generates a calibrating magnetic field, developing an electromagnetic coupling between the one of the calibrating coils and the selected magnetic generator or magnetic field sensor. The selected magnetic generator or magnetic field sensor outputs the electric signal by way of electromagnetic induction. The electric signal is transmitted through the coaxial cables to the electromagnetic coupling switching means, and then from the electromagnetic coupling switching means to the signal processing means.

The signal processing means may comprise a network analyzer, for example. The network analyzer may measure the calibrating input signal and the electric signal to measure a gain (the ratio between the calibrating input signal and the electric signal) and a phase of the apparatus for measuring three-dimensional movement. In this case, the measuring resolution of the magnetic generator and the magnetic field sensors with respect to position can be evaluated from the measured gain when the two objects make relative movement.

The electromagnetic coupling switching means may be used to electrically control the electromagnetic coupling combinations. In this case, the switching means may comprise a coaxial relay, a semiconductor switch, or the like, and the coaxial cables and the electromagnetic coupling switching means may be matched in impedance to each other with substantially the same characteristic impedance (e.g., 50 [Ω]). With this arrangement, the apparatus for measuring three-dimensional movement can operate at high frequencies, and the positional accuracy of the magnetic generator and the magnetic field sensors can be further increased.

The coaxial cables should preferably be of as small a diameter as possible so as not to obstruct the relative movement of the two objects.

The two relatively movable objects, on which the magnetic generators and the magnetic field sensors are mounted, comprise a combination of at least two of a part movable in unison with an upper jaw, a part movable in unison with a lower jaw, a tongue, and an artificial tooth mounted in an oral cavity. The magnetic generators and the magnetic field sensors can be mounted in small, optically concealed locations in the oral cavity or the like of an examinee, because the generators and the sensors are a magnetic type. So as not to obstruct movement, each of the magnetic generators and the magnetic field sensors is in the form of a planar coil, and each of the coaxial cables has a small diameter. Since each of the magnetic generators functions as a marker coil, the positions and directions of each of magnetic generators and the magnetic field sensors can be measured by the apparatus for measuring three-dimensional movement. Thus, six-degree-of-freedom jaw movement can be measured with a positional accuracy of 100 [μm] or less, for example. Therefore, the apparatus for measuring three-dimensional movement can be used for patients with temporomandibular disorder, who need to be accurately checked for jaw movement in dental examination, for measuring jaw movement with higher accuracy and reliability.

Since only the magnetic generators and the coaxial cables are inserted in the oral cavity of the examinee, the burden on the examinee is reduced, and particularly the burden on children and aged people is greatly reduced.

Since both the magnetic generators and the magnetic field sensors are inserted in the oral cavity of the examinee, the apparatus for measuring three-dimensional movement can be reduced in size and cost. The apparatus for measuring three-dimensional movement can therefore easily be introduced into dental clinics, for example, for raising the general standard of dentistry medical treatment.

If the magnetic generators and the coaxial cables are replaced each time the jaw movement of a patient is to be measured, then the apparatus for measuring three-dimensional movement is made more hygienic.

According to the present invention, there is also provided a method of measuring three-dimensional relative movement of at least two objects, comprising the steps of mounting a plurality of magnetic generators on one of the two objects, mounting a plurality of magnetic field sensors on the other object, with the magnetic generators and the magnetic field sensors being paired in at least five combinations; placing a plurality of calibrating coils near the magnetic generators and the magnetic field sensors out of contact therewith, and detecting calibrating magnetic fields generated by the calibrating coils with the magnetic generators and the magnetic field sensors to measure initial positions and initial directions of the magnetic generators and the magnetic field sensors when the two objects are not moving relatively to each other; removing the calibrating coils, and thereafter detecting a measuring magnetic field generated by one of the magnetic generators with one of the magnetic field sensors while electromagnetic coupling combinations between the magnetic generators and the magnetic field sensors are being switched by electromagnetic coupling switching means; and determining relative positions and directions of the magnetic generators with respect to the magnetic field sensors from magnetic fields detected by the magnetic field sensors, and calculating relative movement between the two objects. In this case, the two objects comprise two parts, which move relatively to each other in a living body, for example a combination of at least two of a part movable in unison with an upper jaw, a part movable in unison with a lower jaw, a tongue, and an artificial tooth mounted in an oral cavity. Further, the magnetic generators and the magnetic field sensors can be placed in the oral cavity of an examinee.

BEST MODE FOR CARRYING OUT THE INVENTION

Figure 1:
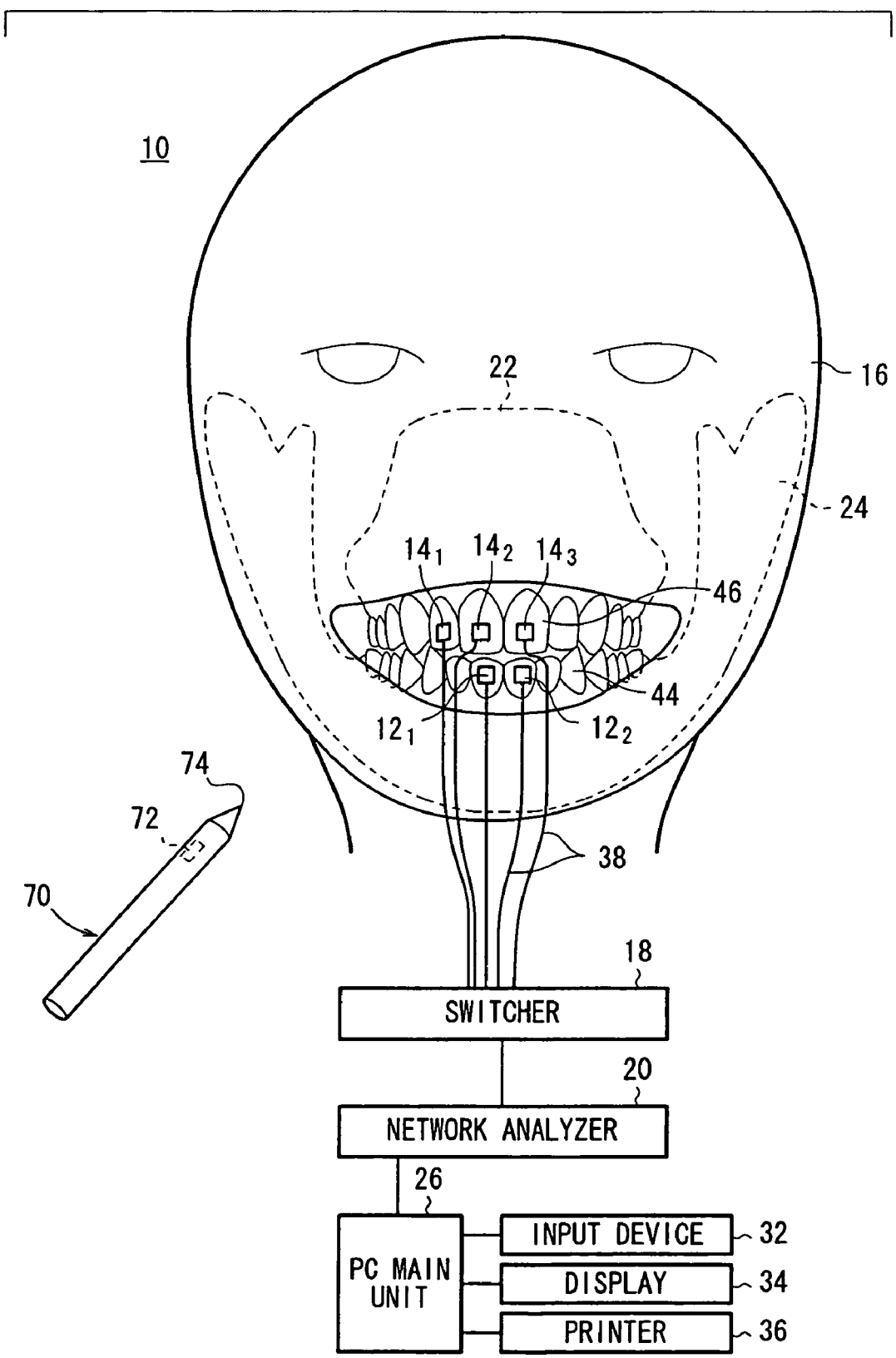
FIG. 1 is a schematic view of a three-dimensional jaw movement measuring apparatus according to an embodiment of the present invention.

FIG. 1 is a schematic view showing an arrangement of a three-dimensional jaw movement measuring apparatus 10 according to an embodiment of the present invention.

Figure 2:
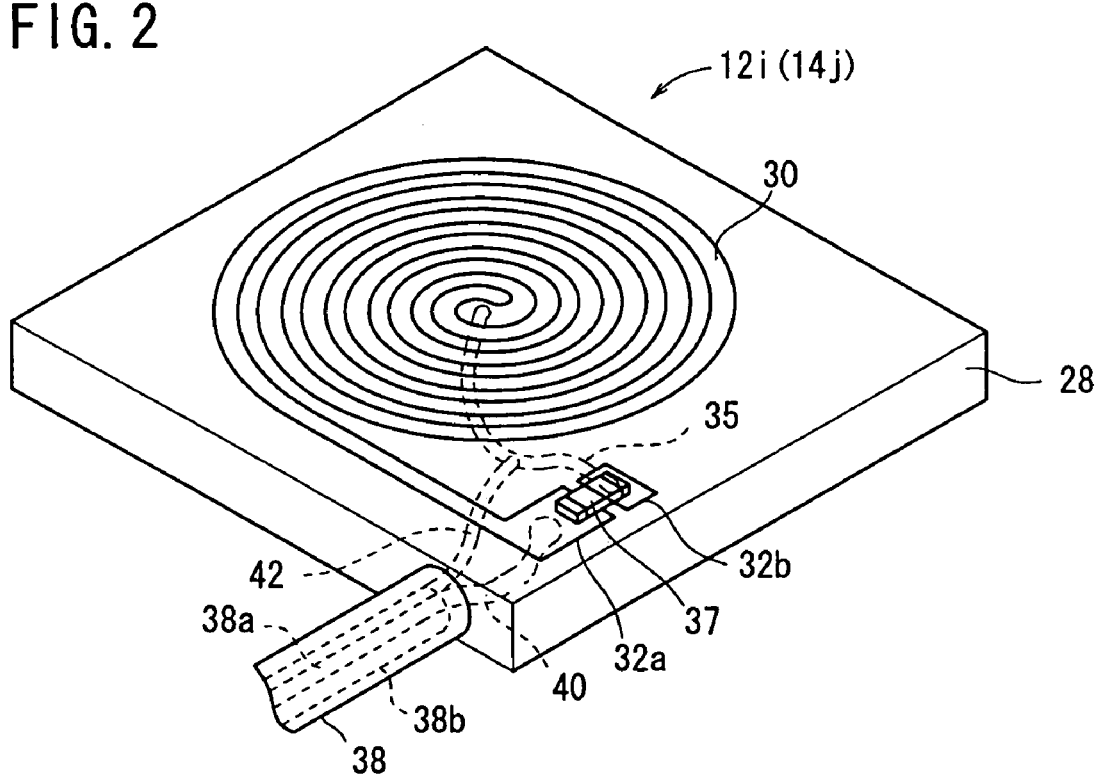
FIG. 2 is a perspective view of a planar coil shown in FIG. 1.
Figure 3:
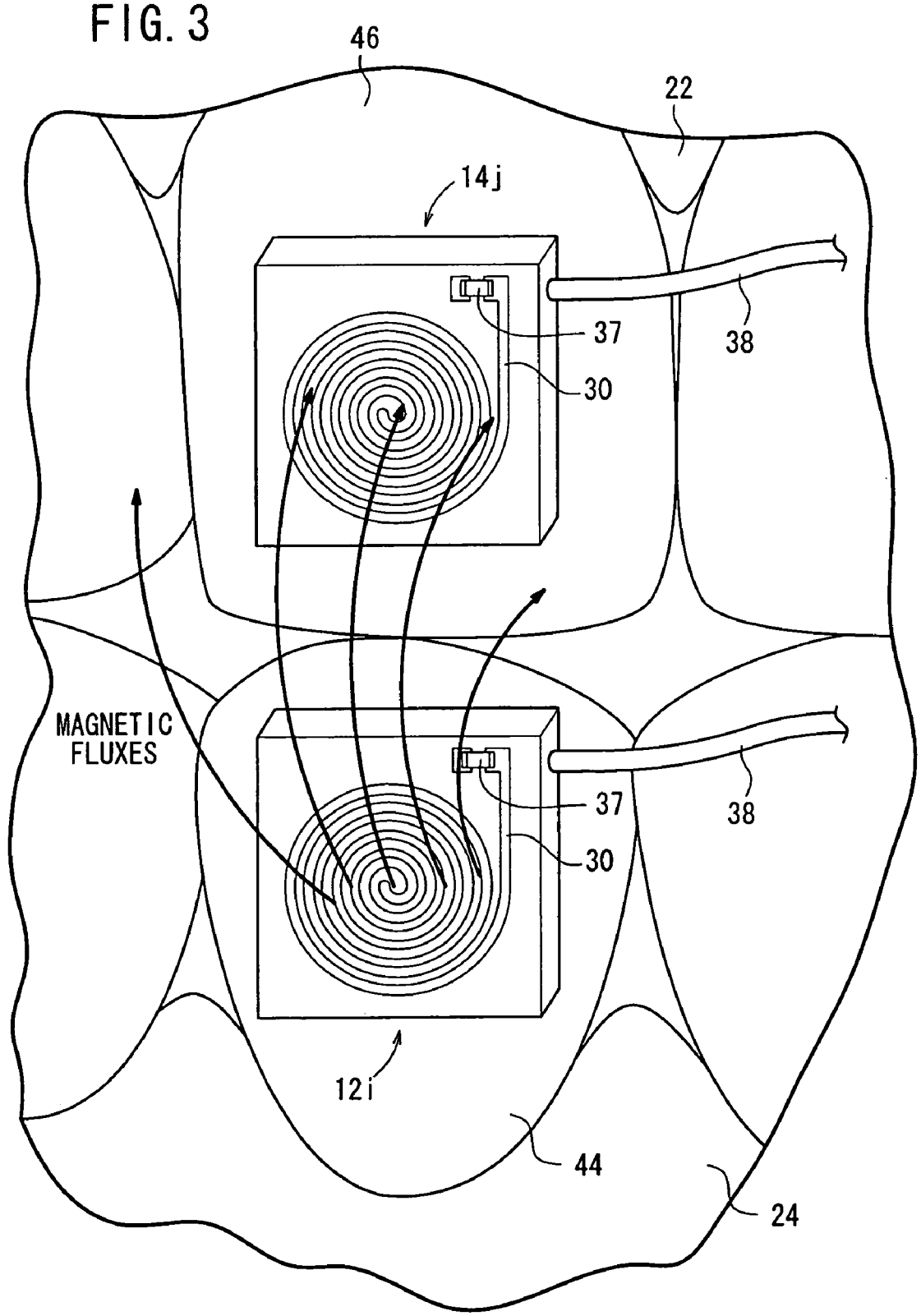
FIG. 3 is an enlarged perspective view of a magnetic generator and a magnetic field sensor shown in FIG. 1.
Figure 4:
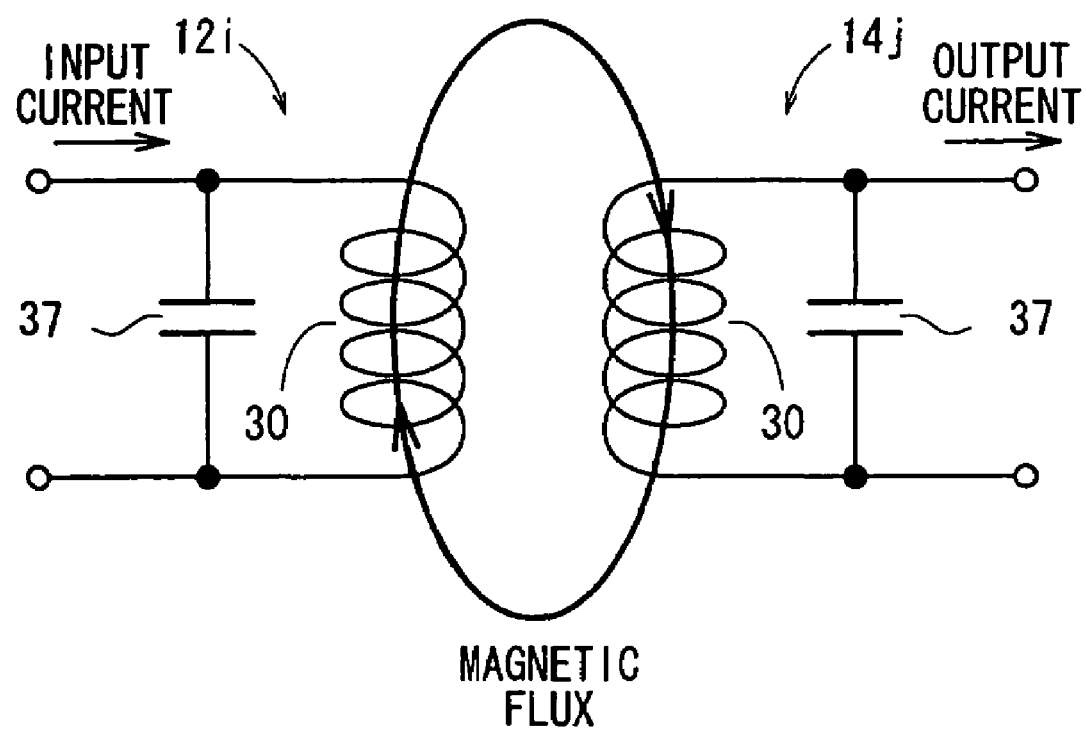
FIG. 4 is a diagram illustrative of an electromagnetic coupling between the magnetic generator and the magnetic field sensor shown in FIG. 3.

FIG. 2 is a perspective view of a magnetic generator 12 and a magnetic field sensor 14 of the three-dimensional jaw movement measuring apparatus 10 shown in FIG. 1. FIG. 3 is a perspective view showing the manner in which the magnetic generator 12 and the magnetic field sensor 14 shown in FIG. 2 are applied respectively to given positions on an examinee 16. FIG. 4 is a diagram showing an equivalent circuit of the magnetic generator $12_i$ and the magnetic field sensor $14_j$ shown in FIG. 2.

As shown in FIGS. 1 through 4, the three-dimensional jaw movement measuring apparatus 10 basically includes a plurality of magnetic generators $12_i$ (i=1, 2 in FIG. 1) attached to given positions on the examinee 16 with an adhesive or the like (not shown), a plurality of magnetic field sensors $14_j$ (j=1 through 3 in FIG. 1) attached to given positions on the examinee 16 with an adhesive or the like (not shown), an electromagnetic coupling switcher 18, a network analyzer 20 connected to the electromagnetic coupling switcher 18, and a personal computer (PC) main unit 26 serving as a signal processing means connected to the network analyzer 20.

Each of the magnetic generators $12_i$ and the magnetic field sensors $14_j$ which detect a magnetic field (magnetic fluxes) generated by the magnetic generators $12_i$ comprises, as shown in FIG. 2, a board 28 made of an insulating material such as epoxy or the like, a spiral planar coil 30 printed as a pattern on the board 28 by the screen printing technology, for example, and a capacitor 37 disposed between an electrode pad 32a on an outer circumferential end of the planar coil 30 and an electrode pad 32b connected to a lead 35 extending from the planar coil 30.

As shown in FIGS. 2 and 4, the capacitor 37 is connected in parallel to the planar coil 30. However, the capacitor 37 may be connected in series to the planar coil 30 (not shown).

The electrode pad 32a shown in FIG. 2 is connected through a lead 40 to a cable core 38a of a coaxial cable 38, whereas the electrode pad 32b is connected through a lead 42 to a shielding wire 38b of the coaxial cable 38.

As shown in FIG. 3, the magnetic generator $12_i$ is fixedly held on a lower jaw tooth 44 of a lower jaw 24 with an adhesive (not shown), which is applied to the surface of the board 28 (the bottom of the board 28 in FIG. 2) that is free of the planar coil 30.

According to the present embodiment, in view of the fact that the magnetic generator $12_i$ is placed in the oral cavity of the examinee 16, the planar coil 30 has a diameter of about 10 [mm] and has about 20 coil turns, with each of the coil turns having a width of about 0.1 [mm] and the coil turns being spaced by about 0.1 [mm].

It has been confirmed from the results of a preliminary experiment that the coaxial cables 38 may preferably be of substantially the same length and may preferably have substantially the same impedance as the impedance of the electromagnetic coupling switcher 18. It has also been confirmed that if the frequency of an electric signal passing through the coaxial cables 38 is up to 10 MHz, then no reflections occur in the electromagnetic coupling switcher 18. It has further been confirmed that if the shielding wires 38b are commonly grounded, then common mode noise can be removed. It has also been confirmed that it is desirable to use very thin coaxial cables having a diameter of about 1.2 [mm] as the coaxial cables 38, thereby minimizing the surface areas of the shielding wires 38b for the purpose of reducing variations in the magnetic field from the magnetic generator $12_i$, the variations being caused by the shielding wires 38b.

The magnetic field sensor $14_j$ is identical in structure to the magnetic generator $12_i$. The magnetic field sensor $14_j$ is fixedly held on an upper jaw tooth 46 of an upper jaw 22 with an adhesive (not shown), which is applied to the surface of the board 28 that is free of the planar coil 30. The coaxial cable 38 is connected to the electromagnetic coupling switcher 18 shown in FIG. 1.

A combination of a magnetic generator $12_i$, which generates magnetic fluxes, and a magnetic field sensor $14_j$, which detects the magnetic fluxes, is selected in advance by the electromagnetic coupling switcher 18, and then the network analyzer 20 supplies a measuring electric signal (input current) to the electromagnetic coupling switcher 18 and, in turn, through the coaxial cable 38 to the selected magnetic generator $12_i$. As shown in FIGS. 3 and 4, the planar coil 30 of the magnetic generator $12_i$ generates magnetic fluxes (indicated by the solid line with the arrows in FIGS. 3 and 4), which link the planar coil 30 of the selected magnetic field sensor $14_j$.

The planar coil 30 of the magnetic field sensor $14_j$ now generates a detecting electric signal (output current) due to electromagnetic induction. The output current is output through the coaxial cable 38 and, in turn, through the electromagnetic coupling switcher 18 to the network analyzer 20.

Since the magnetic field sensor $14_j$ is identical in structure to the magnetic generator $12_i$, as described above, the magnetic field sensor $14_j$ that is fixedly held on the upper jaw tooth 46 may be used as a magnetic generator, and the magnetic generator $12_i$ that is fixedly held on the lower jaw tooth 44 may be used as a magnetic field sensor.

The electromagnetic coupling switcher 18 serves as a switch for selecting a combination of a magnetic generator $12_i$, which generates magnetic fluxes, and a magnetic field sensor $14_j$, which detects the magnetic fluxes. The electromagnetic coupling switcher 18 should preferably comprise a switching device such as a coaxial relay, a semiconductor switch, or the like. In view of reflections, the electromagnetic coupling switcher 18 should preferably be matched in impedance to the coaxial cables 38 with a characteristic impedance (e.g., 50 [Ω]) which is substantially the same as the impedance of the coaxial cables 38.

The network analyzer 20 is a device for supplying a measuring electric signal (input current) to the magnetic generator $12_i$ and receiving a detecting electric signal (output current) from the magnetic field sensor $14_j$. The network analyzer 20 can measure a gain and a phase based on the electromagnetic coupling between the magnetic generator $12_i$ and the magnetic field sensor $14_j$, from the input current and the output current.

As shown in FIG. 1, the PC main unit 26 serves as a signal processing means for determining the position and direction of the magnetic generator $12_i$ with respect to the magnetic field sensor $14_j$ based on the input current and the output current, and calculating in real time a three-dimensional movement of the lower jaw 24 with respect to the upper jaw 22 based on the determined position and direction of the magnetic generator $12_i$ and the shape of the lower jaw (lower jawbone) 24, which is a rigid body.

The PC main unit 26 is connected to an input device 32 such as a keyboard, a mouse, a monitor display 34 such as a CRT display, and a printer 36. Based on the measured results from the network analyzer 20, the PC main unit 26 calculates a relative movement between the upper jaw 22 and the lower jaw 24, and determines the position and direction of the lower jaw 24 with respect to the upper jaw 22.

Figure 5:
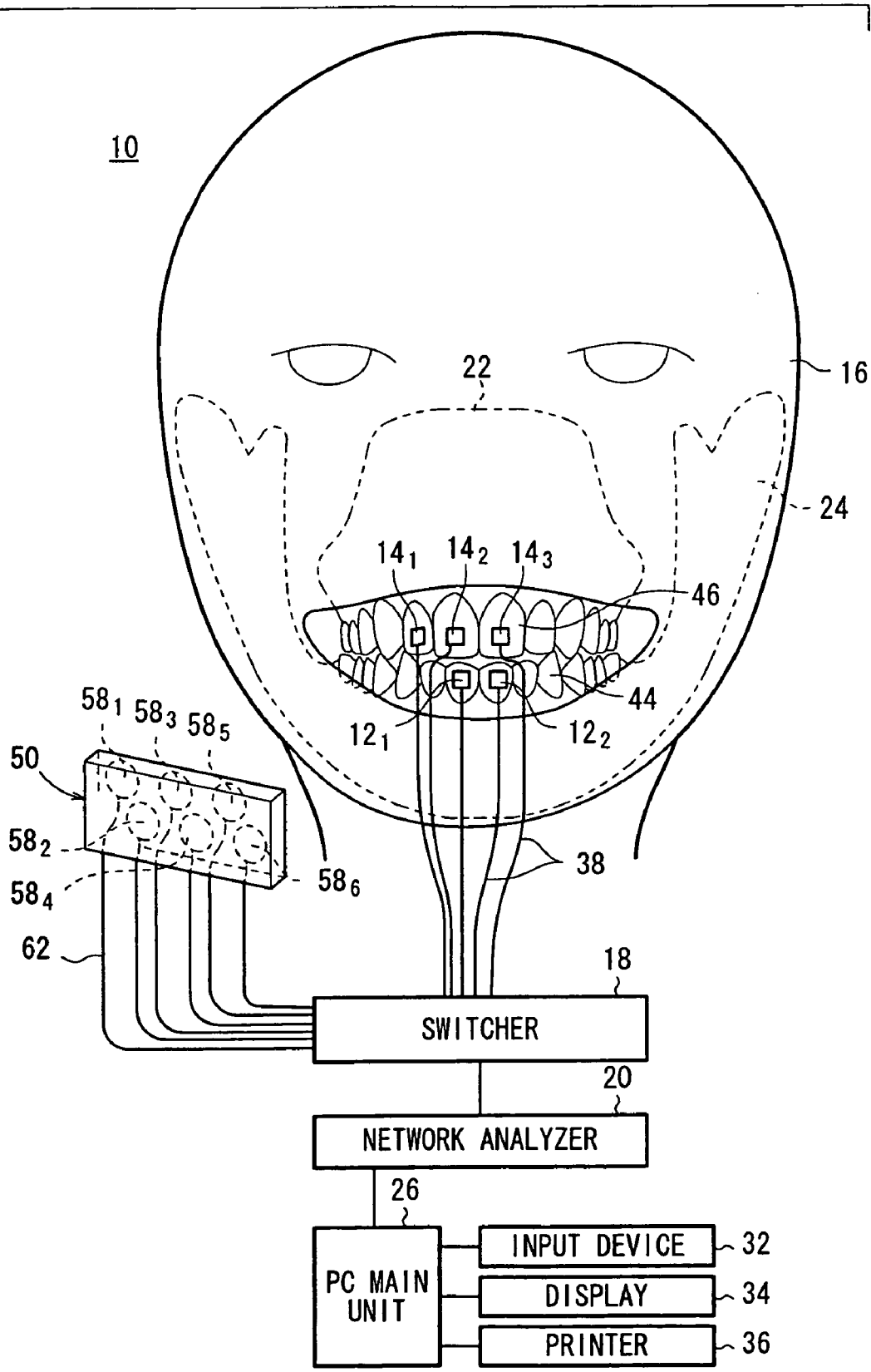
FIG. 5 is a schematic view showing a calibrating coil device placed in the vicinity of an examinee in the three-dimensional jaw movement measuring apparatus shown in FIG. 1.

As shown in FIG. 5, the three-dimensional jaw movement measuring apparatus 10 further includes a calibrating coil device 50 for measuring initial positions of the magnetic generators $12_i$ and the magnetic field sensors $14_j$ before the upper jaw 22 and the lower jaw 24 make a relative movement.

Figure 6:
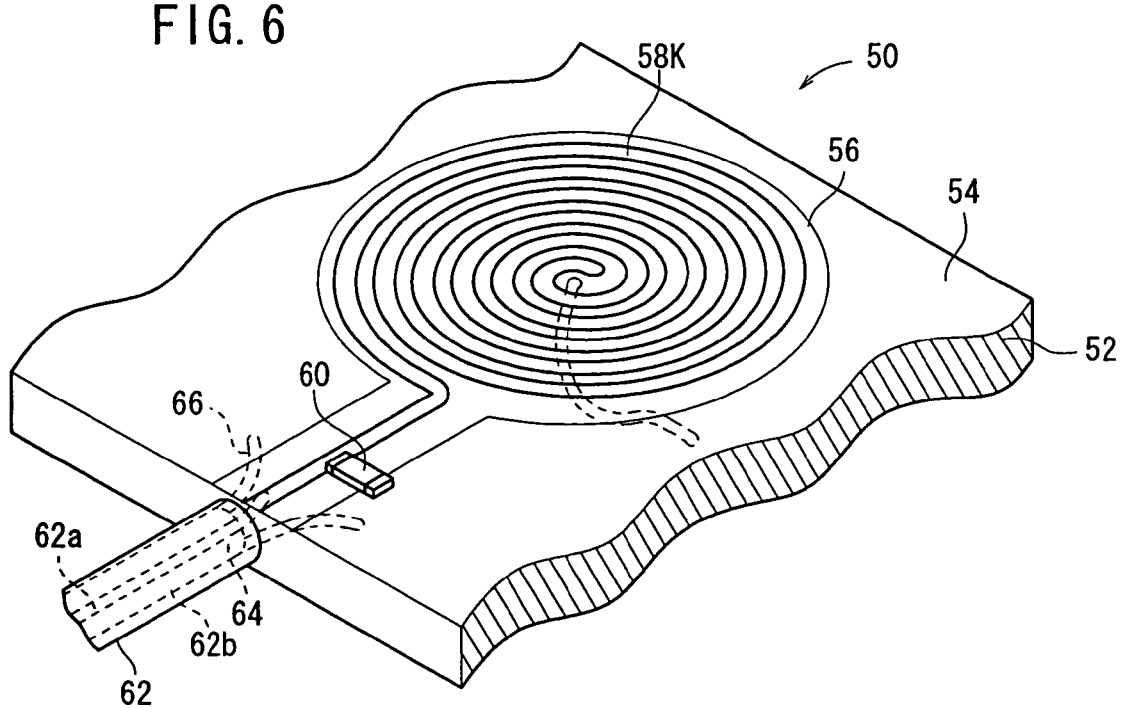
FIG. 6 is an enlarged perspective view of the calibrating coil device shown in FIG. 5.
Figure 7:
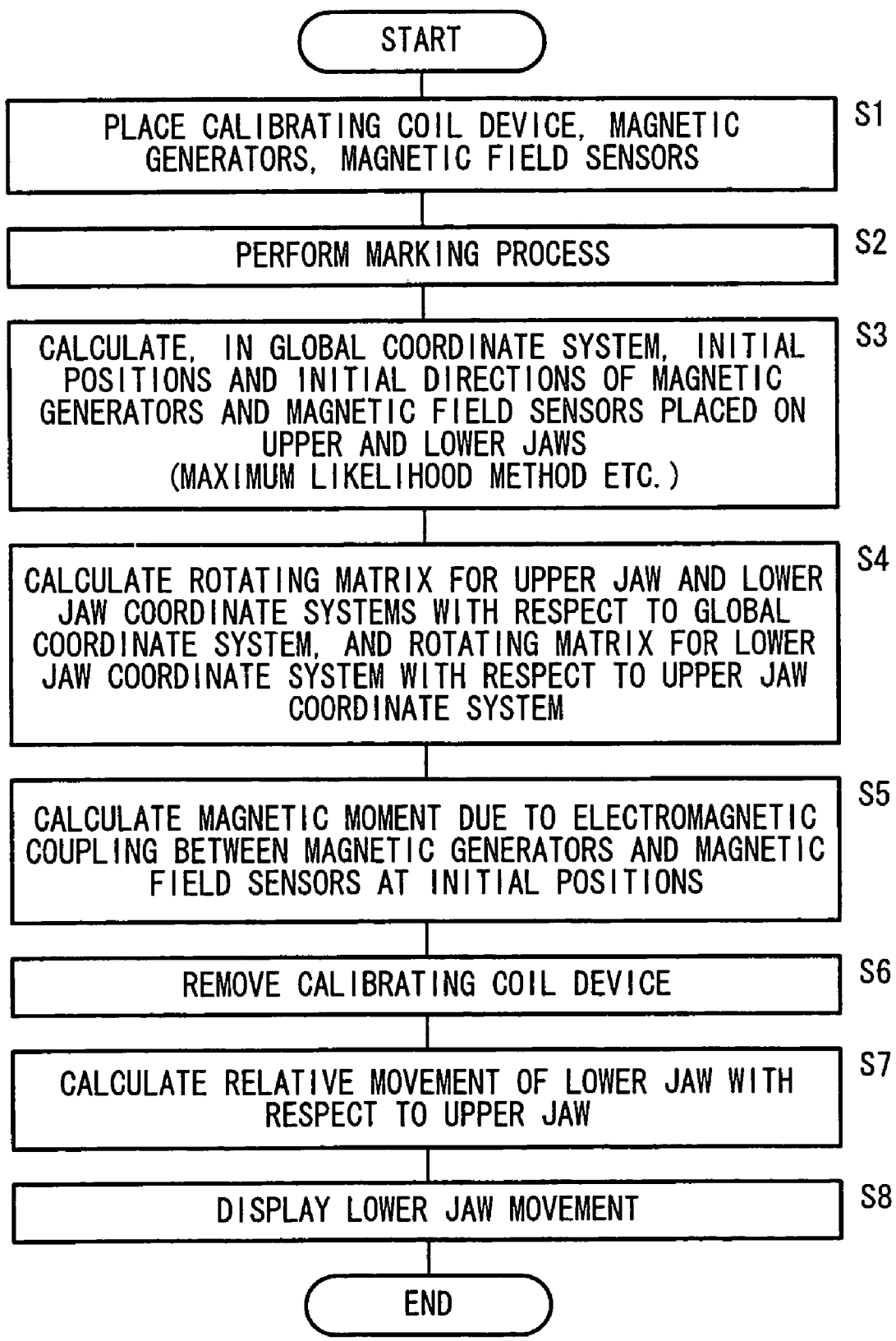
FIG. 7 is a flowchart of a jaw movement measuring process carried out by the three-dimensional jaw movement measuring apparatus shown in FIG. 1.

As shown in FIGS. 5 and 6, the calibrating coil device 50 includes a board 52 made of an insulating material such as epoxy or the like with an electrode pattern 54 formed substantially entirely on the surface of the board 52. The electrode pattern 54 is partially peeled off to provide a plurality of insulating areas 56. The calibrating coil device 50 also has a plurality of spiral planar coils $58_k$ (k=1 through 6 in FIG. 5) printed as a pattern on respective insulating areas 56 by the screen printing technology, for example. A capacitor 60 is connected between an outer circumferential end of each of the planar coils $58_k$ and the electrode pattern 54. The planar coil $58_k$ is connected through a lead 64 to a cable core 62a of a coaxial cable 62, whereas the electrode pattern 54 is connected through a lead 66 to a shielding wire 62b of the coaxial cable 62.

As shown in FIG. 6, the capacitor 60 is connected parallel to the planar coil $58_k$. However, the capacitor 60 may be connected in series to the planar coil $58_k$ (not shown).

As shown in FIG. 5, the calibrating coil device 50 is disposed out of contact with and in the vicinity of the magnetic generators $12_i$ and the magnetic field sensors $14_j$. The planar coils $58_k$ are connected by coaxial cables 62 to the electromagnetic coupling switcher 18.

According to the present embodiment, each of the planar coils $58_k$ has a diameter of about 10 [mm] and has about 10 coil turns, with each of the coil turns having a width of about 0.2 [mm] and the coil turns being spaced by about 0.2 [mm]. The planar coils $58_k$ are disposed on the surface of the board 52 in a staggered pattern at spaced intervals of 20 [mm]. The coaxial cables 62 are identical in structure to the coaxial cables 38. The electrode pattern 54 connected to the shielding wires 62b functions as a common ground electrode for the planar coils $58_k$.

A combination of a planar coil $58_k$ for generating calibrating magnetic fluxes and a magnetic generator $12_i$ or a magnetic field sensor $14_j$ for detecting the calibrating magnetic fluxes is selected in advance by the electromagnetic coupling switcher 18, and then the network analyzer 20 supplies a calibrating electric signal (calibrating input current) to the electromagnetic coupling switcher 18 and, in turn, through the coaxial cable 62 to the selected magnetic generator $12_i$ or magnetic field sensor $14_j$. The planar coil $58_k$ generates calibrating magnetic fluxes (indicated by the solid line with the arrows in FIG. 5), which link the planar coil 30 (see FIG. 2) of the selected magnetic generator $12_i$ or magnetic field sensor $14_j$.

The planar coil 30 of the magnetic generator $12_i$ or magnetic field sensor $14_j$ now generates a detecting electric signal (calibrating output current) due to electromagnetic induction. The calibrating output current is output through the coaxial cable 38 and, in turn, through the electromagnetic coupling switcher 18 to the network analyzer 20.

As shown in FIG. 1, the three-dimensional jaw movement measuring apparatus 10 includes a pointer 70 having a magnetic marker 72 therein, which can be held by a hand of an examiner or the like (not shown) and can be moved around as desired.

The pointer 70 is in the form of a pencil-like rod having a substantially conical pointed tip end 74, with the magnetic marker 72, which comprises a magnet or a magnetic generator, being housed in the pointer 70. The portion of the pointer 70 other than the magnetic marker 72, which housed in the pointer 70 is made of a nonmagnetic, nonconductive material such as a resin or the like.

The PC main unit 26 functions as signal processing means for processing signals output from the network analyzer 20. Based on an application program, which is recorded in advance, the signal processing means calculates in real time the positions of the magnetic generator $12_i$ and the magnetic field sensor $14_j$ according to a repetitive calculating process such as a maximum likelihood process or the like, and also calculates, when necessary, the position of a contact region of the tip end of the freely movable pointer 70 with the magnetic marker 72 housed therein. The signal processing means can also store and register the position of the contact region of the tip end of the pointer 70 as a relative position with respect to the magnetic generator $12_i$ or the magnetic field sensor $14_j$ (a process of marking a feature point of the upper jaw 22 or the lower jaw 24), and read the registered position when necessary.

When the three-dimensional position of the magnetic generator $12_i$ etc. is measured, the PC main unit 26 stores the measured position of the magnetic generator $12_i$ etc. in a RAM and a hard disk, not shown, and displays, based on the stored position, a jaw movement image of a person corresponding to the examinee 16 as a moving image in real time on the monitor display 34.

The three-dimensional jaw movement measuring apparatus 10 according to the present embodiment is basically constructed as described above. Operation of the three-dimensional jaw movement measuring apparatus 10 will be described in detail below with reference to FIGS. 7 through 16.

In step S1, the magnetic generators $12_i$ (i=1, 2) (see FIGS. 1 and 5) and the magnetic field sensors $14_j$ (j=1 through 3) are placed respectively at given positions in the oral cavity of an examinee 16, and the calibrating coil device 50 is placed in the vicinity of the magnetic generators $12_i$ and the magnetic field sensors $14_j$.

At this time, the surfaces of the magnetic generators $12_i$ and the magnetic field sensors $14_j$ that are remote from the planar coils 30 (see FIG. 2), are coated with an adhesive, not shown, and the magnetic generators $12_i$ and the magnetic field sensors $14_j$ are applied to the surfaces of tooth crowns of the examinee 16 with the adhesive.

In FIGS. 1 and 5, each of the magnetic generators $12_i$ is applied to a central incisor or a lateral incisor on the lower jaw 24, and each of the magnetic field sensors $14_j$ is applied to a central incisor or a lateral incisor on the upper jaw 22. However, the positions where the magnetic generators $12_i$ and the magnetic field sensors $14_j$ are applied are not limited to the above positions. Instead, the magnetic generators $12_i$ may be mounted on the upper jaw 22, and the magnetic field sensors $14_j$ may be mounted on the lower jaw 24. Also, the positions where the magnetic generators $12_i$ and the magnetic field sensors $14_j$ are mounted are not limited to upper jaw teeth 46 and lower jaw teeth 44, and additionally may be a combination of at least two of upper jaw teeth 46, lower jaw teeth 44, the tongue, and artificial teeth mounted in the oral cavity.

Then, the magnetic generators $12_i$ and the magnetic field sensors $14_j$ are connected to the electromagnetic coupling switcher 18 through the coaxial cables 38.

The calibrating coil device 50 is placed out of contact with the magnetic generators $12_i$ and the magnetic field sensors $14_j$. Although the calibrating coil device 50 is shown as being spaced from the examinee 16, the calibrating coil device 50 may be placed on the head, the forehead, or one of the cheeks insofar as it is positioned outside of the oral cavity of the examinee 16.

Then, a process of marking a feature point on the upper or lower jaw is performed (step S2).

The process of marking feature points on the upper and lower jaws is a process of setting any desired point on the surface of the upper jaw 22 or the lower jaw 24, e.g., a feature point such as a point at the central fossa of a left or right first molar on the lower jaw 24 or a point near a left or right head of the lower jaw 24, as relative coordinates with respect to the planar coils 30 of the magnetic generators $12_i$ mounted at given positions on the lower jaw 24.

More specifically, the process of marking feature points on the upper and lower jaws is a process of having the PC main unit 26 recognize and register (store) the relative position (relative three-dimensional position) of any desired point on the upper jaw 22 with respect to the positions of the planar coils 30 of the magnetic field sensors $14_j$ mounted at given positions on the upper jaw 22, and the relative position (relative three-dimensional position) of any desired point on the lower jaw 24 with respect to the positions of the planar coils 30 of the magnetic generators $12_i$ mounted at given positions on the lower jaw 24.

According to the above process, in order to set any desired point (a desired point, a feature point, or a representative point) on the lower jaw 24, for example, the examiner or the like removes the pointer 70 (see FIG. 1) from a pointer holder, not shown, and brings the tip end 74 of the pointer 70 into contact with a given position on the row of teeth on the lower jaw, e.g., the central fossa in the occlusal surface of a first molar.

Magnetic fluxes generated by the magnetic marker 72 link the planar coils 30 of the magnetic generators $12_i$, causing these planar coils 30 to generate electric signals (induced voltage) due to electromagnetic induction. The electric signals are then output through the coaxial cables 38 to the electromagnetic coupling switcher 18. The electromagnetic coupling switcher 18 successively selects the coaxial cables 38 connected to the planar coils 30, outputting the electric signals through the network analyzer 20 to the PC main unit 26.

Based on the electric signals, the PC main unit 26 determines the three-dimensional coordinate position and direction of the central fossa in the occlusal surface of the first molar with respect to the positions of the planar coils 30, from the outputs of the planar coils 30 according to a maximum likelihood process or the like to be described later on.

Actually, while the tip end 74 of the pointer 70 is held in contact with the central fossa in the occlusal surface of the first molar of the examinee 16, the examiner clicks, via an input device, on a displayed message "CONTACTED BY POINTER WITH MAGNETIC MARKER" on the screen of the monitor display 34 according to the displayed information on the monitor display 34. From the magnetic fluxes detected by the planar coils 30, the position of the magnetic marker 72 in the pointer 70 is determined, and the position of the tip end 74 of the pointer 70 is determined. In this case, the position of the tip end 74 represents the position of the central fossa in the occlusal surface of the first molar.

In this manner, the relative positions of the central fossae in the occlusal surfaces of the left and right first molars are determined, and stored and registered in the hard disk of the PC main unit 26. According to the same process, other feature points on the lower jaw 24, e.g., several points such as points near the left and right heads of the lower jaw 24, are marked, and their relative positions with respect to the positions of the planar coils 30 are stored and registered. Consequently, movement of the magnetic generators $12_i$ associated with movement of the lower jaw 24, and movement of the marked points can simultaneously be measured.

The positions of any desired points on the upper jaw 22 and the lower jaw 24 can simply be measured without the need for X-ray CT and an optical means. Therefore, those positions can be measured without irradiating the examinee 16 with X-rays, and a large mechanical structure, such as a position detecting process using an optical means, does not need to be inserted into the oral cavity of the examinee 16.

Even if the examinee 16 moves the head or jaws while marking desired points (feature points, e.g., points at the central fossae in the left and right first molars on the lower jaw or points near the left and right heads of the lower jaw) on the lower jaw 24, since the relative positions of the desired points are determined based on the results measured after the examinee 16 has moved the head or jaws, the marking process is performed with accuracy.

When desired points are marked on the lower jaw 24 with the pointer 70 (relative positions thereof are obtained), since the desired points are touched with the tip end 74 of the pointer 70 and the coordinate positions of the desired points are stored and registered, the coordinate positions of only points exposed on the surface of the examinee 16 can be registered.

Actually, however, it is also necessary to measure movement of points inside of the examinee 16. The positions of those points can be calculated by the PC main unit 26 and then registered. For example, points near the left and right heads of the lower jaw (slightly in front of tragi) are pointed on the skin with the pointer 70, and points that are shifted by 20 [mm] inwardly from a straight line interconnecting the left and right points that have been pointed with the pointer 70 and stored, are calculated by the PC main unit 26. In this manner, the points (corresponding to the points on the left and right heads of the lower jaw) can be registered.

After having completed the process of registering the relative positions of feature points of the shape of the lower jaw 24, the examiner or the like returns the pointer 70 to the pointer holder, not shown.

In step S3, the magnetic fluxes generated by the planar coils $58_k$ of the calibrating coil device 50 are measured with the planar coils 30 of the magnetic generators $12_i$ and the magnetic field sensors $14_j$, and initial positions and initial directions of the magnetic generators $12_i$ and the magnetic field sensors $14_j$ are calculated from the measured results. The initial positions and initial directions of the magnetic generators $12_i$ and the magnetic field sensors $14_j$ represent positions and directions of the magnetic generators $12_i$ and the magnetic field sensors $14_j$ at a time when the lower jaw 24 does not make relative movement with respect to the upper jaw 22 and when the lower jaw 24 is not opened with respect to the upper jaw 22 as shown in FIG. 5.

Prior to the description of a process of calculating the initial positions and the initial directions, a process of measuring the magnetic fluxes from the planar coils $58_k$ with the planar coils 30 of the magnetic generators $12_i$ and the magnetic field sensors $14_j$ will be described below.

First, the electromagnetic coupling switcher 18 selects a planar coil $58k$, which is supplied with a calibrating electric signal (input current) from the network analyzer 20, and a planar coil 30, which detects the magnetic fluxes generated by the planar coil $58k$. The network analyzer 20 then supplies an alternating current to the planar coil $58_k$ selected by the electromagnetic coupling switcher 18.

The alternating current should preferably have a frequency up to 10 [MHz] in view of the impedance of the coaxial cables 38, 62. In this embodiment, the alternating current has a high frequency ranging from 1 [MHz] to 2 [MHz].

If the alternating current is supplied to the planar coil $58_5$, for example, then the planar coil $58_5$ generates calibrating magnetic fluxes as AC magnetic fluxes. The calibrating magnetic fluxes link the magnetic generators $12_i$ and the magnetic field sensors $14_j$, which are disposed in the oral cavity of the examinee 16. The planar coils 30 of the magnetic generators $12_i$ and the magnetic field sensors $14_j$ generate detecting electric signals (induced voltages) due to electromagnetic induction, thereby allowing the induced currents to flow through the coaxial cables 38 to the electromagnetic coupling switcher 18.

The electromagnetic coupling switcher 18 outputs the detecting electric signal (induced current) from a selected planar coil 30 to the network analyzer 20. The network analyzer 20 determines a gain and phase in the electromagnetic coupling between the planar coil $58_k$ and the planar coil 30 from the amplitudes and phases of the calibrating electric signal and the detecting electric signal, and outputs the obtained gain and phase to the PC main unit 26.

The electromagnetic coupling switcher 18 changes combinations of the planar coils $58_k$ and the planar coils 30, thereby switching between electromagnetic coupling combinations.

In FIGS. 1 and 5, the calibrating coil device 50 has five planar coils $58_1$ through $58_5$, and a total of five planar coils 30 are disposed in the oral cavity of the examinee 16. Therefore, calibrating magnetic fluxes generated from the planar coil $58_1$ link the five planar coils 30 of the magnetic generators $12_1$, $12_2$ and the magnetic field sensors $14_1$, $14_2$, $14_3$. There are thus five electromagnetic coupling combinations available for the planar coil $58_l$. Since the magnetic generators $12_i$ function as magnetic field sensors with respect to the calibrating magnetic fluxes from the planar coils $58k$, initial positions and directions of the magnetic generators $12_i$ can be determined in terms of an absolute coordinate system to be described below.

When the electromagnetic coupling switcher 18 switches between and selects from among the planar coils $58_1$ through $58_5$, a total of 25 electromagnetic coupling combinations can be obtained. Therefore, the network analyzer 20 outputs the measured results with respect to the 25 electromagnetic coupling combinations to the PC main unit 26.

From the supplied measured results, the PC main unit 26 calculates initial positions and initial directions of the respective magnetic generators $12_i$ and the respective magnetic field sensors $14_j$ in terms of an absolute coordinate system.

Figure 8:
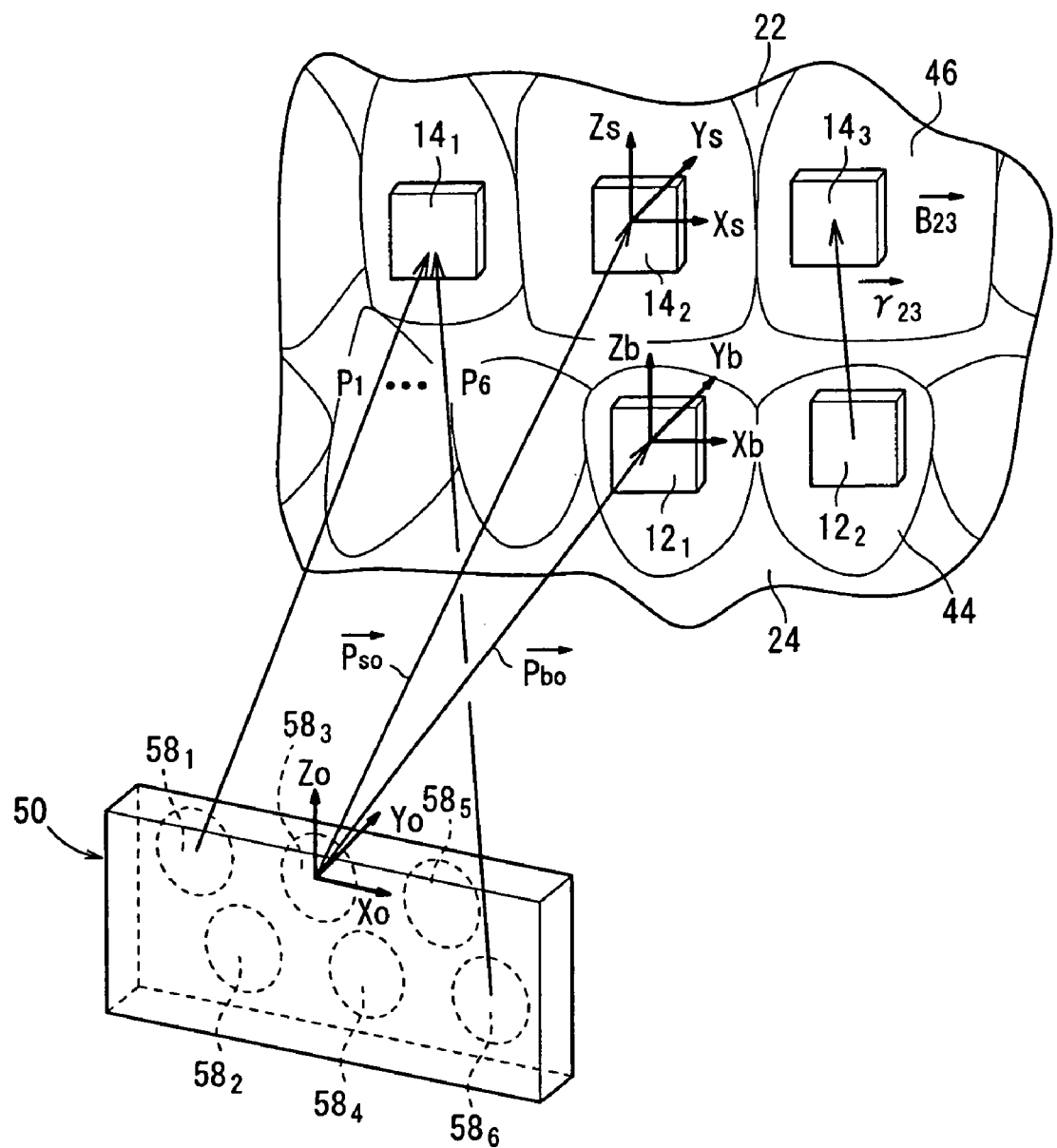
FIG. 8 is a view showing the positions and directions of the calibrating coil device, the magnetic generators, and the magnetic field sensors.

The origin of the absolute coordinate system may be located anywhere. In FIG. 8, for brevity, the origin of the absolute coordinate system $X_0Y_0Z_0$ is placed at the center of the spiral planar coil $58_3$ of the calibrating coil device 50. This position of the origin is applicable throughout the description which follows. The absolute coordinate system $X_0Y_0Z_0$ has an $X_0$ axis and a $Z_0$ axis, which are coordinate axes extending along the surface of the planar coil $58_3$ (see FIG. 6), and a $Y_0$ axis, which is a coordinate axis extending perpendicularly to the planar coil $58_3$.

The initial positions and initial directions of the magnetic generators $12_i$ and the magnetic field sensors $14_j$ in step S3 are calculated as follows: First, as shown in FIG. 9, position vectors $p_1$ through $p_6$ from one of the planar coils 30 of the magnetic generators $12_i$ and the magnetic field sensors $14_j$ (in FIG. 8, the planar coil of the magnetic field sensor $14_1$) to respective planar coils $58_k$ are determined.

Figure 9:
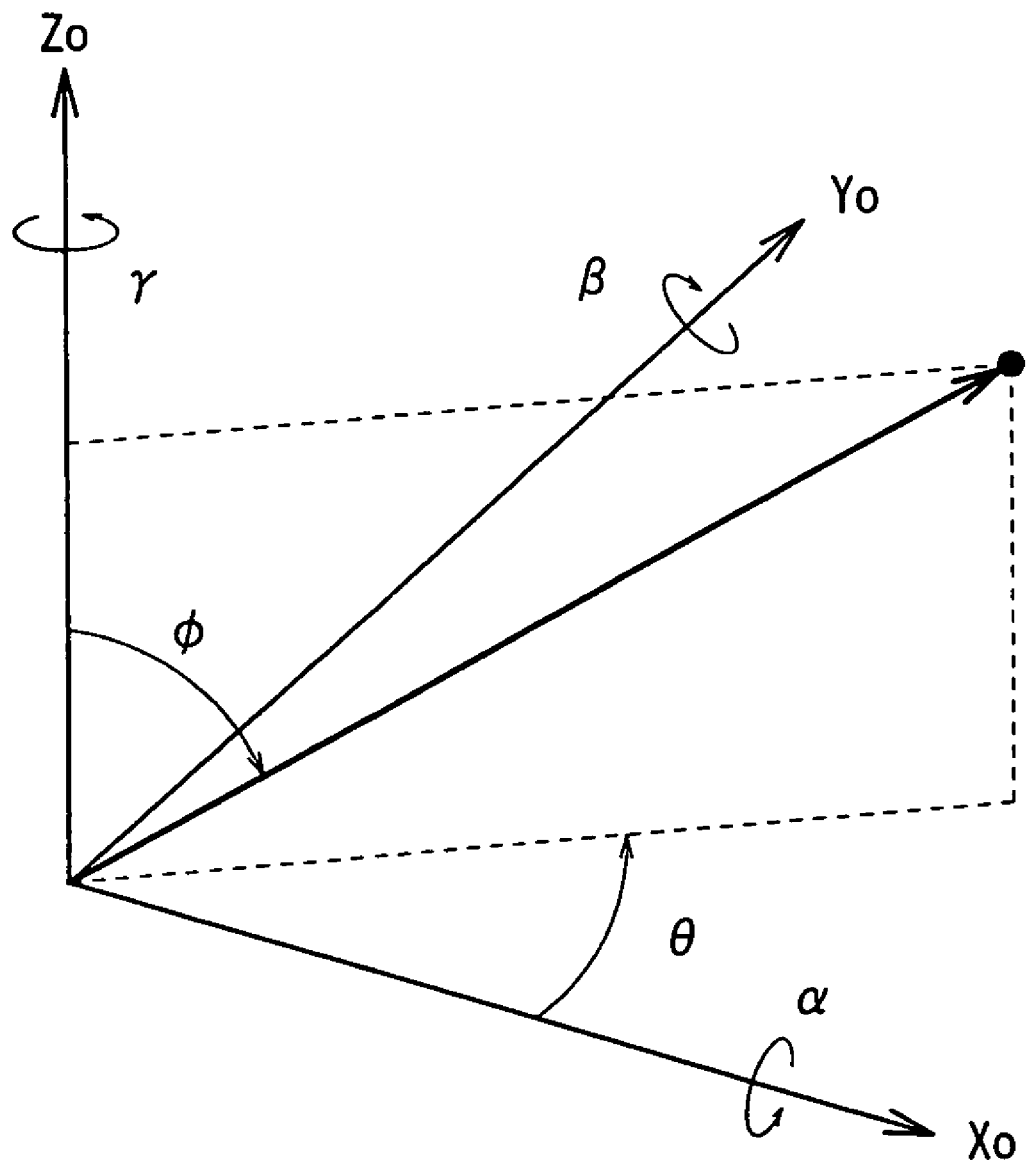
FIG. 9 is a diagram showing a coordinate system (absolute coordinate system) and rotational angles of the calibrating coil device shown in FIG. 8.

Parameters relative to the positions and direction angles (attitude angles, rotational angles) of the planar coil 30 are represented by five-degree-of-freedom information (x, y, z, θ, φ) shown in FIG. 9. The vectors $p_1$ through $p_6$ are thus represented as $p_1$ through $p_6$(x, y, z, θ, φ).

If measured magnetic fluxes from the planar coils $58k$, which are detected by the planar coil 30, are represented by $B_{mk}$ and calculated magnetic fluxes of the flux density from the planar coil 30 due to the dipoles of the planar coils $58k$, whose magnetic moments are known, are represented by $B_{ck}$, then respective parameters of the vectors $p_1$ (x, y, z, θ, φ) through $p_6$ (x, y, z, θ, φ) are determined from the measured magnetic fluxes $B_{mk}$ and calculated magnetic fluxes $B_{ck}$ according to the maximum likelihood process or the like by equation (1) shown below. In the equation (1), k represents the number of planar coils $58_k$, k=1 through 6. For brevity, the symbol (arrow) representing a vector is omitted below.

$$\Sigma(B_{mk}-B_{ck})^2=0 \text{ or a minimal value} \tag{1}$$

Calculations for determining the initial position and initial direction of each planar coil 30 according to the maximum likelihood process based on the least-square method of the equation (1) will be described in detail below.

First, the equation (1) is regarded as an evaluating function S(p) according to the following equation (2):

$$S(p)=S(p_1 \text{ through } p_6)=\Sigma(B_{mk}-B_{ck})^2=0 \text{ or a minimal value} \tag{2}$$

In the equation (2), the various values are represented as follows:

$$B_{ck}=(1/4\pi\mu)\times[\Sigma\{(-M_k/p_k^3)+(3(M_k\cdot p_k)p_k/p_k^5)\}] \quad (3)$$

where "·" in $(M_k\cdot r_k)$ and $(M_k\cdot r_k)$ indicates the inner product of a vector;

vector $p_k$: the positional vector between each planar coil $58_k$ and the planar coil 30; and vector $M_k$: the magnetic moment (known) in each planar coil $58_k$.

If the evaluating function S(p) according to the equation (2) thus defined takes a minimal value at the vector p=q, then the following equation (4) holds where m represents the number of parameters described later:

$$(\partial S(p)/\partial p_i)|_{p=q}=0 (i=1, 2, \ldots m) \quad (4)$$

By substituting the equation (2) into the equation (4) and expanding the equation (4), the following equation (5) is obtained with the range of $\Sigma$ being n=1 through m:

$$\Sigma(\partial^2 S/\partial p_i\partial p_n)\Delta p_n=-(\partial^2 S/\partial p_i), (i=1, 2, \ldots m) \quad (5)$$

The equation (5) represents simultaneous equations according to a determinant of m lines and n columns. The equation (5) is solved for the vector $\Delta p_n$, and the vector q is determined as an optimum solution from vector $p^{(k+1)}$=vector $p^k$+vector $\Delta p_n$.

Considering the fact that the magnetic field is proportional to the cube of the distance, by determining a first-order derivative of the magnetic fields $B_{mk}$, $B_{ck}$ with respect to the distance, and applying the maximum likelihood method only to the first-order derivative and the measured magnetic field $B_{mk}$, the accuracy can be increased.

The initial position and initial direction have been calculated above with respect to the planar coil 30 of the magnetic field sensor $14_1$. However, the initial positions and initial directions of other planar coils 30 can also be calculated using the measured magnetic field $B_{mk}$.

If the calculation of the equation (1) does not converge or if the solution of a parameter is unnatural with respect to nearby locus even though the calculation of the equation (1) converges, then the solution at the point may be excluded, and the calculation may be repeated.

In step S4, the initial positions and initial directions of the magnetic generators $12_i$ and the magnetic field sensors $14_j$ that are calculated in step S3 and expressed in terms of the absolute coordinate system $X_0Y_0Z_0$ (see FIGS. 8 through 10), are expressed in terms of the coordinate system $X_sY_sZ_s$ of the upper jaw 22 (upper jaw coordinate system) shown in FIGS. 8, 10 through 12 and the coordinate system $X_bY_bZ_b$ of the lower jaw 24 (lower jaw coordinate system) shown in FIGS. 8, 10, 12, 13.

The origin of the upper jaw coordinate system $X_sY_sZ_s$ may be set to any position on the upper jaw 22. In FIG. 8, the origin of the upper jaw coordinate system $X_sY_sZ_s$ is shown as being set to the central position of the magnetic field sensor $14_2$ (the center of the spiral region of the planar coil 30 shown in FIG. 2). The upper jaw coordinate system $X_sY_sZ_s$ has an $X_s$ axis and a $Z_s$ axis, which are coordinate axes extending along the surface of the planar coil 30, and a $Y_s$ axis, which is a coordinate axis extending perpendicularly to the planar coil 30.

The origin of the lower jaw coordinate system $X_bY_bZ_b$ may be set to any position on the lower jaw 24. In FIG. 8, the origin of the lower jaw coordinate system $X_bY_bZ_b$ is shown as being set to the central position of the magnetic generator $12_1$ (the center of the spiral region of the planar coil 30 shown in FIG. 2). The lower jaw coordinate system $X_bY_bZ_b$ has an $X_b$ axis and a $Z_b$ axis, which are coordinate axes extending along the surface of the planar coil 30, and a $Y_b$ axis, which is a coordinate axis extending perpendicularly to the planar coil 30.

If the positional vector $P_{js}$ (j=1 through 3) of a desired point in the upper jaw coordinate system $X_sY_sZ_s$ is expressed as a positional vector $P_{js0}$ in the absolute coordinate system $X_0Y_0Z_0$, then the positional vector $P_{js}$ is expressed according to the following equation (6) based on the positional vector $P_{s0}$ of the upper jaw coordinate system $X_sY_sZ_s$ with respect to the absolute coordinate system $X_0Y_0Z_0$ and a coordinate transformation matrix (rotating matrix) $R_s$ for transforming the absolute coordinate system $X_0Y_0Z_0$ into the upper jaw coordinate system $X_sY_sZ_s$:

$$P_{js}=R_s(P_{js0}-P_{s0}) \quad (6)$$

In FIG. 9, the position of the magnetic field sensor $14_1$ is shown as being expressed by a positional vector $P_{1s}$ in the upper jaw coordinate system $X_sY_sZ_s$ and by a positional vector $P_{1s0}$ in the absolute coordinate system $X_0Y_0Z_0$.

If rotational angles about an $X_0$ axis, a $Y_0$ axis, and a $Z_0$ axis shown in FIG. 9 are represented respectively by $\alpha$, $\beta$ and $\gamma$, then the rotating matrix $R_s$ is expressed according to the following equation (7):

$$Rs = \begin{bmatrix} \cos\gamma & -\sin\gamma & 0 \\ \sin\gamma & \cos\gamma & 0 \\ 0 & 0 & 1 \end{bmatrix} \begin{bmatrix} 1 & 0 & 0 \\ 0 & \cos\alpha & -\sin\alpha \\ 0 & \sin\alpha & \cos\alpha \end{bmatrix} \begin{bmatrix} \cos\beta & 0 & -\sin\beta \\ 0 & 1 & 0 \\ -\sin\beta & 0 & \cos\beta \end{bmatrix} \quad (7)$$

Figure 10:
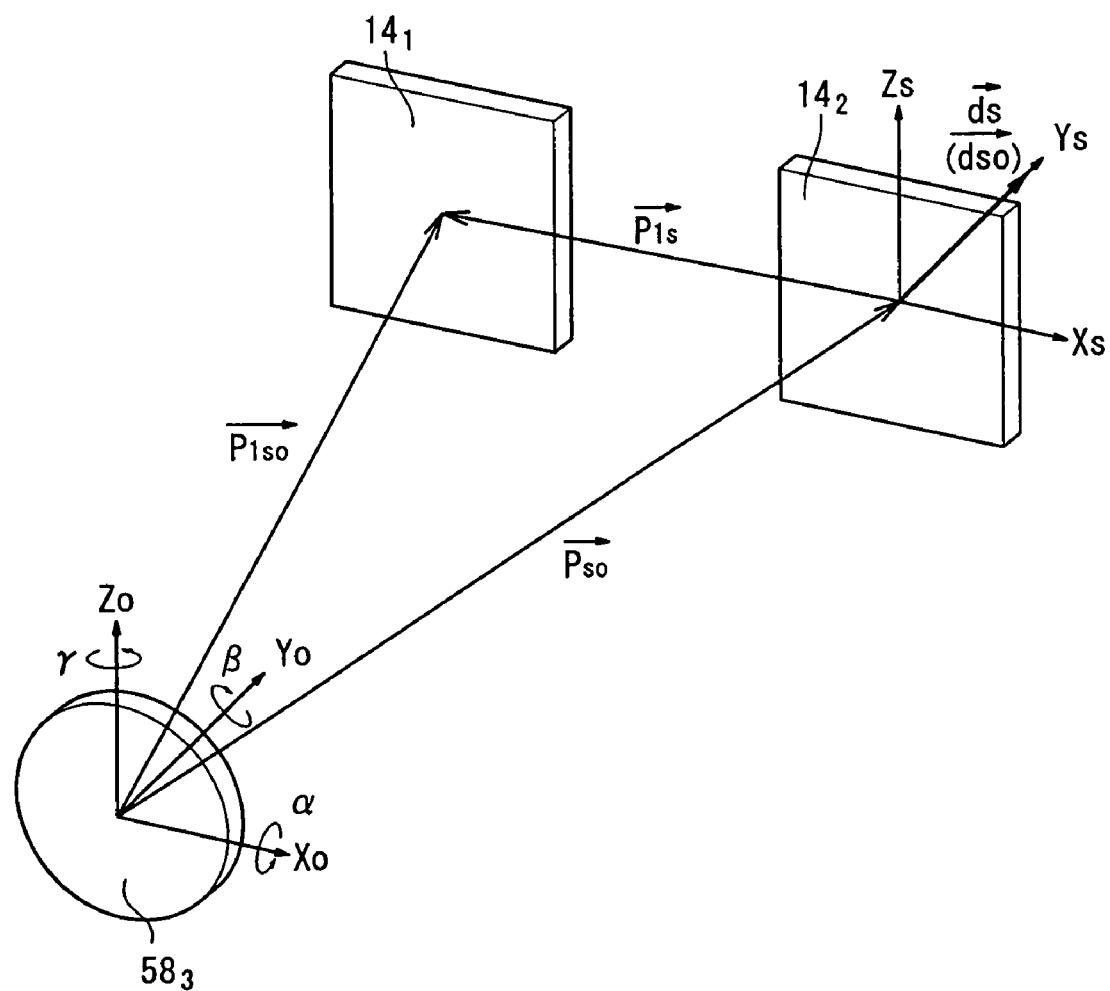
FIG. 10 is a view showing the positions and directions of a planar coil of the calibrating coil device and magnetic field sensors.
Figure 11:
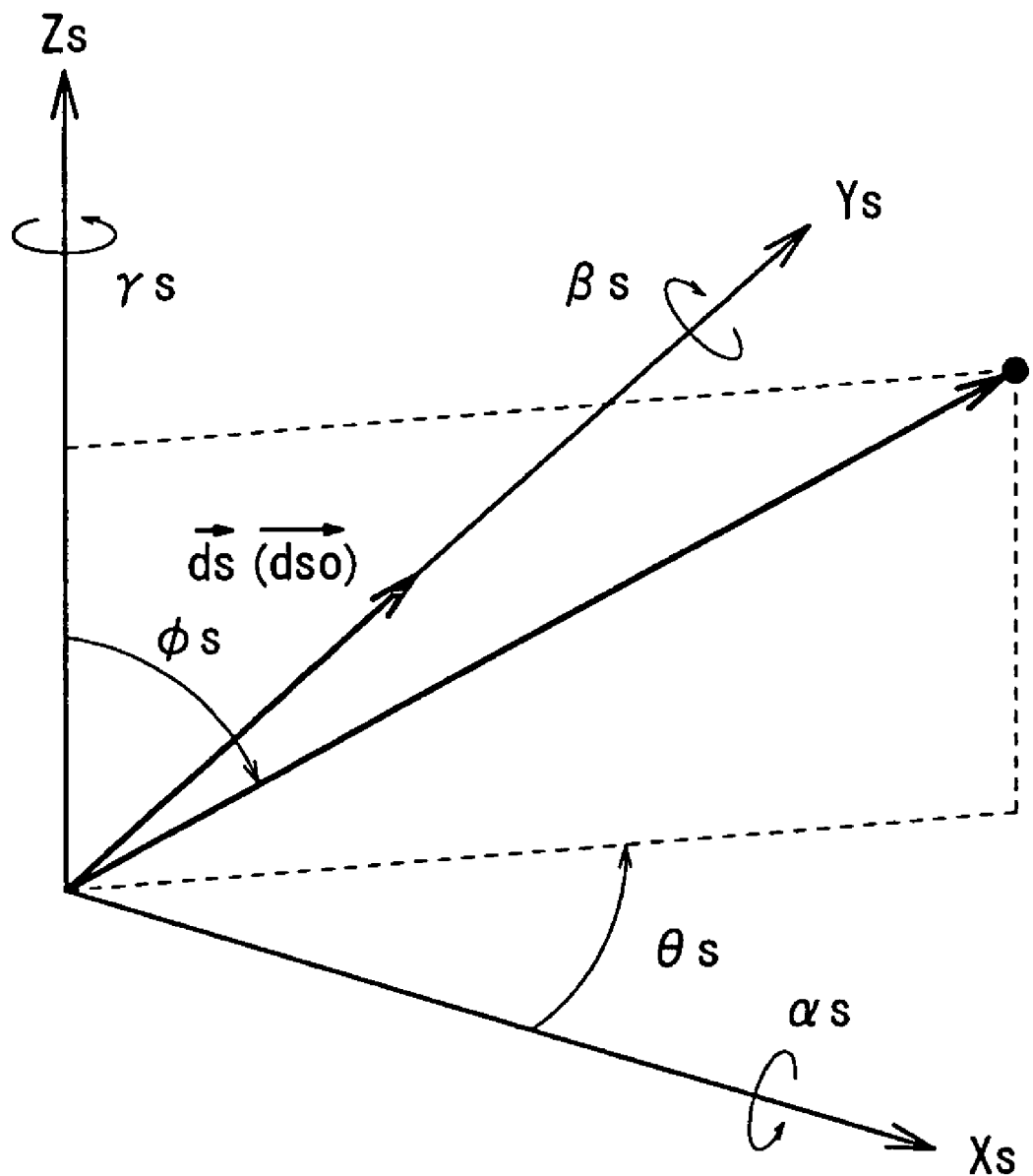
FIG. 11 is a diagram showing a coordinate system (upper jaw coordinate system) of the magnetic sensors shown in FIG. 10.

If a unit vector extending perpendicularly to the magnetic field sensor $14_2$ and parallel to the $Y_s$ axis is represented by $d_{s0}$ in the absolute coordinate system $X_0Y_0Z_0$, as shown in FIG. 10, then the unit vector, as transformed into a unit vector $d_s$ in the upper jaw coordinate system $X_sY_sZ_s$ (see FIGS. 10 and 11), is expressed according to the following equation (8):

$$d_s=R_s d_{s0} \quad (8)$$

Figure 12:
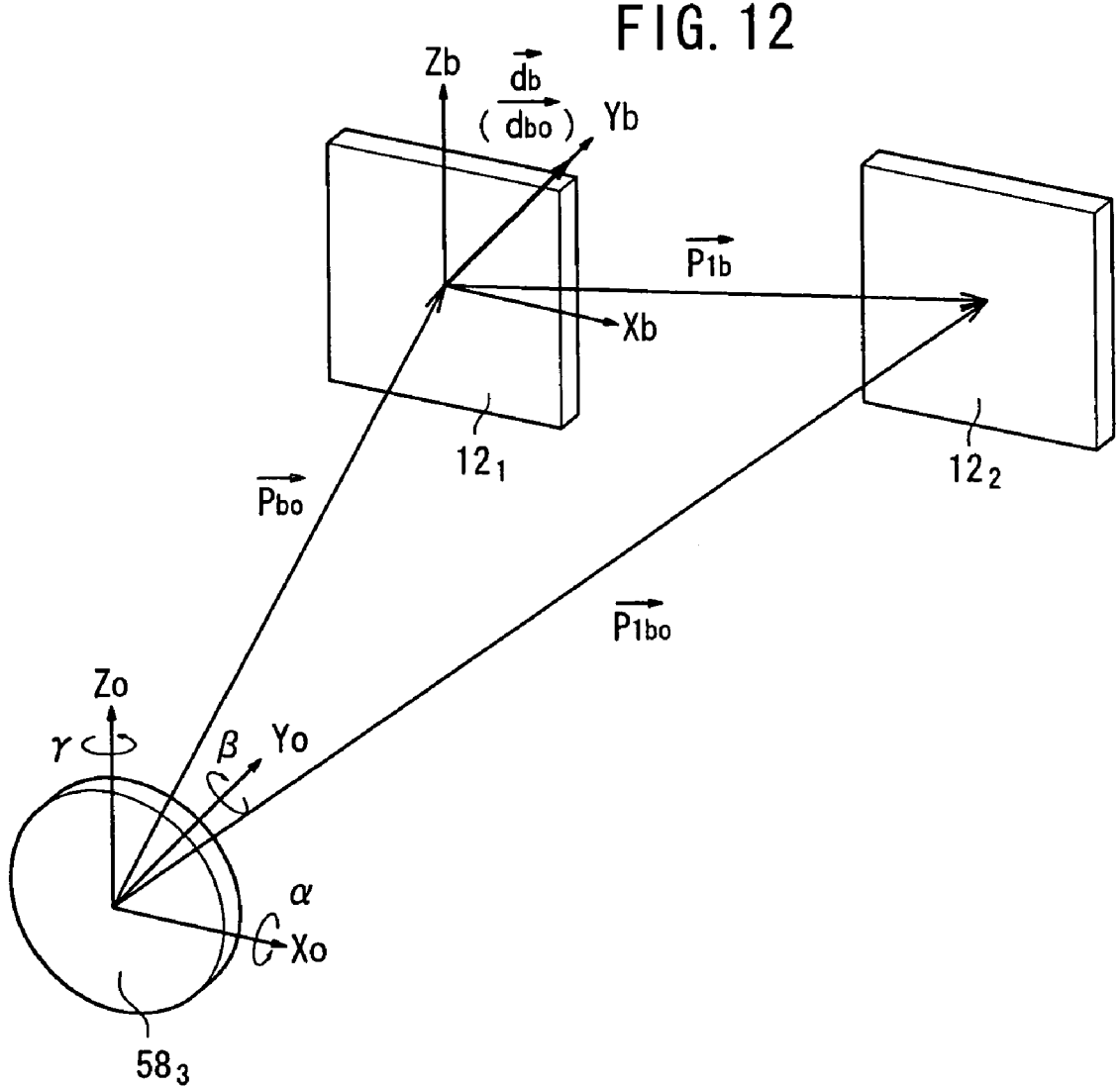
FIG. 12 is a view showing the positions and directions of the planar coil of the calibrating coil device and magnetic generators.

If the positional vector $P_{ib}$ (i=1, 2) of a desired point in the lower jaw coordinate system $X_bY_bZ_b$ is expressed as a positional vector $P_{ib0}$ in the absolute coordinate system $X_0Y_0Z_0$ shown in FIGS. 8 and 12, then the positional vector $P_{ib}$ is expressed according to the following equation (9) based on the positional vector $P_{b0}$ of the lower jaw coordinate system $X_bY_bZ_b$ with respect to the absolute coordinate system $X_0Y_0Z_0$ and a coordinate transformation matrix (rotating matrix) $R_b$ for transforming the absolute coordinate system $X_0Y_0Z_0$ into the lower jaw coordinate system $X_bY_bZ_b$:

$$P_{ib}=R_b(P_{ib0}-P_{b0}) \quad (9)$$

The rotating matrix $R_b$ is expressed in the same manner as by the equation (7).

Figure 13:
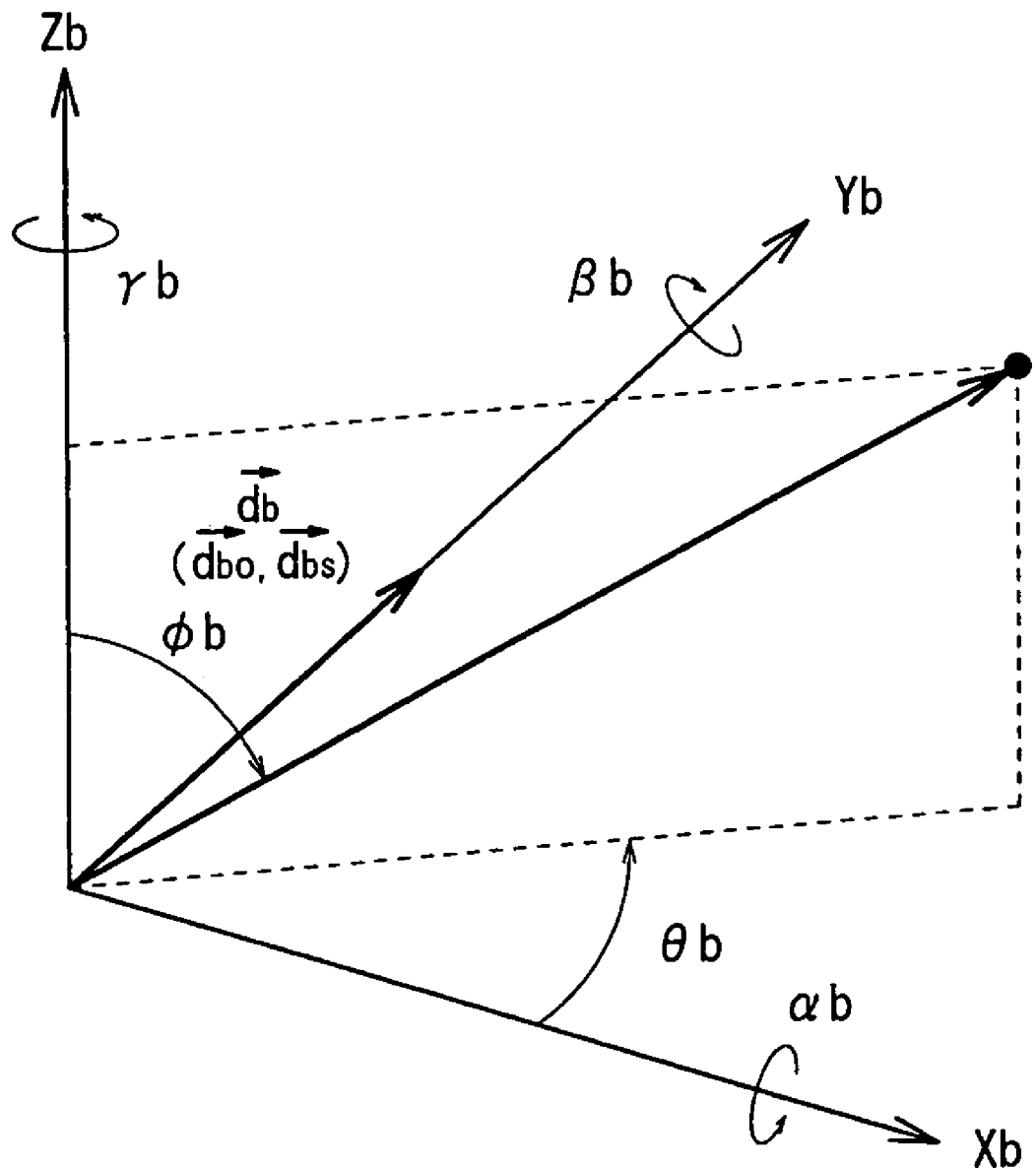
FIG. 13 is a diagram showing a coordinate system (lower jaw coordinate system) of the magnetic generators shown in FIG. 12.

If a unit vector extending perpendicularly to the magnetic generator $12_1$ and parallel to the $Y_b$ axis is represented by $d_{b0}$ in the absolute coordinate system $X_0Y_0Z_0$, as shown in FIGS. 12 and 13, then the unit vector as transformed into a unit vector $d_b$ in the lower jaw coordinate system $X_bY_bZ_b$ is expressed according to the following equation (10):

$$d_b=R_b d_{b0} \quad (10)$$

The rotating matrix $R_s$ may be determined, under the condition that the unit vector $d_{js}$ in the upper jaw coordinate system $X_sY_sZ_s$ is parallel to the $Y_s$ axis and, when the vector $P_{js}$ is projected onto an $X_sZ_s$ plane, not shown, the projected vector is parallel to a component of the vector $P_{js}$ in the $X_s$ direction, by constructing nonlinear simultaneous equations with respect to the equation (6), using the initial positions and initial directions of the respective planar coils 30 which have been calculated in step S3, and performing iterative calculations according to the Newton method, for example, with respect to the simultaneous equations.

The rotating matrix $R_b$ may also be determined, under the condition that the unit vector $d_b$ in the lower jaw coordinate system $X_bY_bZ_b$ is parallel to the $Y_b$ axis and, when the vector $P_{ib}$ is projected onto an $X_bZ_b$ plane, not shown, the projected vector is parallel to a component of the vector $P_{ib}$ in the $X_b$ direction, by constructing nonlinear simultaneous equations with respect to the equation (6), using the initial positions and initial directions of the respective planar coils 30 which have been calculated in step S3, and performing iterative calculations according to the Newton method, for example; with respect to the simultaneous equations.

Then, a coordinate transformation matrix (rotating matrix) $R_{bs}$ for transforming the upper jaw coordinate system $X_sY_sZ_s$ into the lower jaw coordinate system $X_bY_bZ_b$ is determined from the rotating matrixes $R_s$, $R_b$ according to the following equation (11):

$$R_{bs} = R_b R_s^{-1} \qquad (11)$$

where $R_s^{-1}$ represents an inverse matrix of the rotating matrix $R_s$.

Using these rotating matrixes $R_s$, $R_b$, and $R_{bs}$, the initial positions and initial directions of the respective planar coils 30 which have been measured in the absolute coordinate system $X_0Y_0Z_0$ using the calibrating coil device 50 can be expressed in the upper jaw coordinate system $X_sY_sZ_s$ or the lower jaw coordinate system $X_bY_bZ_b$ according to the equations (6) and (9).

Then, in step S5, magnetic moments $M_i$ of the respective magnetic generators $12_i$ are determined based on the electromagnetic coupling between the magnetic generators $12_i$ and the magnetic field sensors $14_j$ in the initial positions and initial directions.

In step S5, a magnetic generator $12_i$, through which an alternating current flows, and a magnetic field sensor $14_j$, which detects magnetic fluxes, are selected in advance by the electromagnetic coupling switcher 18. The network analyzer 20 supplies an alternating current through the electromagnetic coupling switcher 18 to the planar coil 30 of the magnetic generator $12_i$. Magnetic fluxes generated by the alternating current are detected as an induced current by the planar coil 30 of the selected magnetic field sensor $14_j$. The induced current is then output through the electromagnetic coupling switcher 18 to the network analyzer 20.

FIG. 13 typically shows the manner in which the magnetic fluxes from the magnetic generator $12_2$ are detected by the magnetic field sensor $14_3$.

If the flux density $B_{ij}$ (i=1, 2, j=1 through 3 in FIG. 8) of the magnetic fluxes generated by the magnetic generator $12_i$ is detected by the magnetic field sensor $14_j$, then the flux density $B_{ij}$ is expressed by the following equation (12) from a vector $r_{ij}$ between the magnetic generator $12_i$ and the magnetic field sensor $14_j$, a unit vector $d_j$ normal to the magnetic field sensor $14_j$ which is expressed in the upper jaw coordinate system $X_sY_sZ_s$, and a magnetic moment $M_i$ of the magnetic generator $12_i$:

$$B_{ij} = (1/4\pi\mu) \times \{(-M_i/r_{ij}^3) + (3(M_i \cdot r_{ij}) \cdot r_{ij}^5)\} \cdot d_j \qquad (12)$$

where $M_i$ is expressed as $M_i$=(the magnitude $M_{ij}$ of the magnetic moment $M_i$)·(the unit vector $d_j$ normal to the magnetic generator $12_i$).

FIG. 8 shows that the magnetic field sensor $14_3$ detects a flux density $B_{23}$ of the magnetic fluxes generated by the magnetic generator $12_2$.

From the equation (12), the magnitude $M_{ij}$ of the magnetic moment $M_i$ is determined according to the following equation (13):

$$M_{ij} = B_{ij}/[(1/4\pi\mu) \times \{(-d_i/r_{ij}^3) + (3(d_i \cdot r_{ij}^5))\} \cdot d_{j1}] \qquad (13)$$

Actually, the flux density $B_{ij}$ is measured a plurality of times, and an average value of the magnetic moments $M_i$ is calculated based on the measured results.

Then, in step S6, the coaxial cable 62 is detached from the electromagnetic coupling switcher 18, and the calibrating coil device 50 and the coaxial cable 62 are moved to a location which is free of the effect of the magnetic fluxes generated by the magnetic generators $12_i$.

In step S7, the relative position and attitude angle of the lower jaw 24 with respect to the upper jaw 22 are determined based on a change in the electromagnetic coupling between the magnetic generators $12_i$ and the magnetic field sensors $14_j$ at the time the lower jaw 24 has moved with respect to the upper jaw 22.

First, the electromagnetic coupling switcher 18 selects the planar coil 30 of a magnetic generator $12_i$, through which a measuring electric signal (input current) flows from the network analyzer 20, and the planar coil of a magnetic field sensor $14_j$, which detects magnetic fluxes generated by the planar coil 30 of the magnetic generator $12_i$. Then, the network analyzer 20 supplies an alternating current to the planar coil 30 of the magnetic generator $12_i$ which has been selected by the electromagnetic coupling switcher 18.

As with the calibrating electric signal in step S3, the alternating current should preferably be an alternating current having a frequency up to 10 [MHz] in view of the impedance of the coaxial cable 38. As an example, an alternating current having a high frequency in the range from 1 [MHz] to 2 [MHz] is employed.

When the alternating current is supplied to one, shown in FIG. 3, for example, of the planar coils 30 of the respective magnetic generators $12_i$, the supplied alternating current generates measuring magnetic fluxes as alternating magnetic fluxes, and the measuring magnetic fluxes link the planar coils 30 of the magnetic field sensors $14_j$ which are placed in the oral cavity of the examinee 16. The planar coils 30 generate detecting electric signals (output currents) due to electromagnetic induction, and the output currents flow through the coaxial cables 38 to the electromagnetic coupling switcher 18.

The electromagnetic coupling switcher 18 outputs the output current from a selected planar coil 30 to the network analyzer 20. The network analyzer 20 determines a gain and a phase in the electromagnetic coupling between the magnetic generator $12_i$ and the magnetic field sensor $14_j$, from the amplitudes and phases of the input current and the output current, and outputs the gain and the phase to the PC main unit 26.

The electromagnetic coupling switcher 18 changes combinations of the magnetic generators $12_i$ and the magnetic field sensors $14_j$, thereby switching between electromagnetic coupling combinations. In FIGS. 1 and 5, since two magnetic generators $12_1$, $12_2$ and three magnetic field sensors $14_1$, $14_2$, $14_3$ are placed in the oral cavity of the examinee 16, there are six electromagnetic coupling combinations. In step S7, the network analyzer 20 outputs measured results about the six electromagnetic coupling combinations to the PC main unit 26.

If the positional vector between the magnetic generator $12_i$, which generates magnetic fluxes, and the magnetic field sensor $14_j$, which detects the flux density $B_{ij}$ of the magnetic fluxes, is represented by $r_{ij}$ (see FIG. 8), then the flux density $B_{ij}$ is expressed according to the above equation (12) from the unit vector $d_j$ normal to the magnetic field sensor 14$_j$ and the magnetic moment $M_i$ of the magnetic generator 12$_i$. The positional vector $r_{ij}$ is expressed according to the following equation (14) from the positional vector $P_{bs}$ between the upper jaw coordinate system $X_s Y_s Z_s$ and the lower jaw coordinate system $X_b Y_b Z_b$, the positional vector $P_{is}$ of a desired point which is expressed in the upper jaw coordinate system $X_s Y_s Z_s$, the positional vector $P_{ib}$ of a desired point which is expressed in the lower jaw coordinate system $X_b Y_b Z_b$, and a rotating matrix $R_{bs}$:

$$r_{ij} = P_{bs} + R_{bs}^{-1} P_{ib} - P_{is} \quad (14)$$

where $R_{bs}^{-1}$ represents an inverse matrix of the rotating matrix $R_{bs}$. The rotating matrix $R_{bs}$ is expressed according to the following equation (15) from rotational angles $\alpha_s$, $\beta_s$ and $\gamma_s$ respectively about the $X_s$ axis, the $Y_s$ axis, and the $Z_s$ axis of the upper jaw coordinate system $X_s Y_s Z_s$ shown in FIG. 11:

$$R_{bs} = \begin{bmatrix} \cos\gamma_s & -\sin\gamma_s & 0 \\ \sin\gamma_s & \cos\gamma_s & 0 \\ 0 & 0 & 1 \end{bmatrix} \begin{bmatrix} 1 & 0 & 0 \\ 0 & \cos\alpha_s & -\sin\alpha_s \\ 0 & \sin\alpha_s & \cos\alpha_s \end{bmatrix} \begin{bmatrix} \cos\beta_s & 0 & -\sin\beta_s \\ 0 & 1 & 0 \\ -\sin\beta_s & 0 & \cos\beta_s \end{bmatrix} \quad (15)$$

The unit vector $d_b$ (see FIG. 13) which is expressed in the lower jaw coordinate system $X_b Y_b Z_b$ and which extends perpendicularly to the magnetic generator 12$_1$ and parallel to the $Y_b$ axis is also expressed as a unit vector $d_{bs}$ according to the following equation (16) by transforming it into the upper jaw coordinate system $X_s Y_s Z_s$ using the rotating matrix $R_{bs}$:

$$d_{bs} = R_b d_b \quad (16)$$

The rotating matrix $R_{bs}$ according to the equation (15) is determined, and the obtained result is substituted into the equations (14) and (16), thereby determining the positional vector $P_{bs}$ and the unit vector $d_{bs}$.

If measured magnetic fluxes from the planar coils 30 of the respective magnetic generators 12$_i$ which are detected by the planar coils 30 of the respective magnetic field sensors 14$_j$ are represented by $B_{ij}$ and calculated magnetic fluxes of the flux density from the planar coil 30 of the magnetic generator 12$_i$ whose magnetic moments are known, are represented by $B_{ci}$, then parameters of the vector $r_{ij}$ are determined from the measured magnetic fluxes $B_{ij}$ and calculated magnetic fluxes $B_{ci}$ according to the maximum likelihood process or the like by the following equation (17) shown below.

$$\Sigma(B_{ij} - B_{ci})^2 = 0 \text{ or a minimal value} \quad (17)$$

The equation (17) is regarded as an evaluating function $S(p)$ according to the following equation (18):

$$S(p) = S(r_{ij}) = \Sigma(B_{ij} - B_{ci})^2 = 0 \text{ or a minimal value} \quad (18)$$

In the equation (18), the flux density $B_{ij}$ is the same as $B_{ij}$ in the equation (12) and the flux density $B_{ci}$ is expressed according to the following equation (19):

$$B_{ci} = (1/4\pi\mu) \times [\Sigma\{(-M_i/r_{ij}^3) + (3(M_i \cdot r_{ij}) r_{ij}/r_{ij}^5)\}] \quad (19)$$

where "·" in $(M_i \cdot r_{ij})$ and $(M_i \cdot r_{ij})$ indicates the inner product of a vector; and vector $M_i$: the magnetic moment (known) in the planar coil 30 of each magnetic generator 12$_i$.

If the evaluating function $S(r_{ij})$ according to the equation (18) thus defined takes a minimal value at the vector $r_{ij} = q$, then the following equation (20) holds where m represents the number of parameters described later:

$$(\partial S(r_{ij})/\partial r_{ij})|_{r_{ij}=q} = 0 (i, j = 1, 2, \ldots m) \quad (20)$$

By substituting the equation (18) into the equation (20) and expanding the equation (20), the following equation (21) is obtained with the range of $\Sigma$ being n=1 through m:

$$\Sigma(\partial^2 S/\partial p_i \partial p_n)\Delta p_n = -(\partial^2 S/\partial p_i), (i = 1, 2, \ldots m) \quad (21)$$

The equation (21) represents simultaneous equations according to a determinant of m lines and m columns. The equation (21) is solved for the vector $\Delta p_n$, and the vector q is determined as an optimum solution from vector $p^{(i+1)}$=vector $p^i$+vector $\Delta p_n$.

Considering the fact that the magnetic field is proportional to the cube of the distance, by determining a first-order derivative of the magnetic fields $B_{ij}$, $B_{ci}$ with respect to the distance, and applying the maximum likelihood method only to the first-order derivative and the measured magnetic field $B_{ij}$, the accuracy can be increased.

The initial position and initial direction have been calculated above with respect to the planar coil 30 of the magnetic field sensor 14$_1$. However, the initial positions and initial directions of other planar coils 30 can also be calculated using the measured magnetic field $B_{ij}$.

If the calculation of the equation (21) does not converge or if the solution of a parameter is unnatural with respect to nearby locus even though the calculation of the equation (21) converges, then the solution at the point may be excluded, and the calculation may be repeated.

Then, in step S8, the relative movement of the lower jaw 24 with respect to the upper jaw 22 which has been determined in step S7 is converted into an image on the monitor display 34 as representing the movement of the lower jaw 24, and the image is displayed. The movement of the lower jaw 24 can be recorded on a hard disk, a digital video disk, or the like, and hence can be reproduced as often as needed. Furthermore, since the movement of the lower jaw 24 can be played back in a slow mode, a still mode, or a high-speed mode, the jaw movement can be diagnosed from various viewpoints.

Some experimental examples will be described below with reference to FIGS. 14 through 16.

Figure 14:
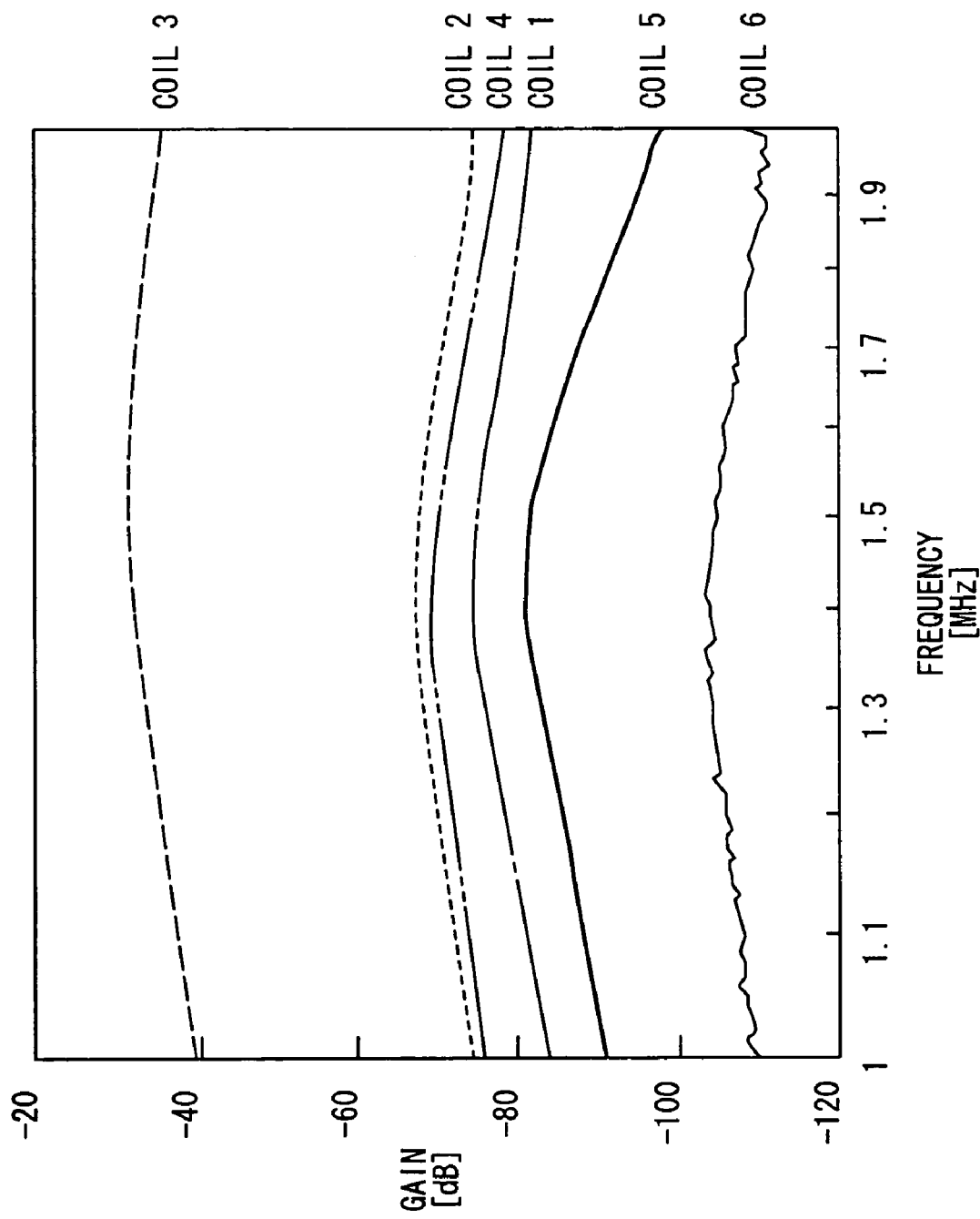
FIG. 14 is a characteristic diagram showing the frequency characteristics of gains of the three-dimensional jaw movement measuring apparatus shown in FIG. 5.

FIG. 14 shows frequency characteristics of gains between the planar coils 58$_k$ and the planar coils 30 of the magnetic generators 12$_i$ and the magnetic field sensors 14$_j$ when magnetic fluxes are generated from the planar coils 58$_k$ of the calibrating coil device 50 which is disposed in the vicinity of the examinee 16, with the three magnetic generators 12$_i$ (12$_1$ through 12$_3$) being mounted on the tooth crown surfaces of the central and lateral incisors on the upper jaw 22 and the three magnetic field sensors 14$_i$ (14$_1$ through 14$_3$) being mounted on the tooth crown surfaces of the central and lateral incisors on the lower jaw 24.

Coils 1 through 3 represent the measured results of the planar coils 30 of the magnetic generators 12$_1$ through 12$_3$, respectively, and coils 4 through 6 represent the measured results of the planar coils 30 of the magnetic field sensors 14$_1$ through 14$_3$, respectively.

In this experimental example, the ratios between calibrating electric signals (alternating currents) of 1 through 2 [MHz] which flow through the respective planar coils 58$_k$ and induced currents (output currents) detected by the coils 1 through 6 are output as the gains from the network analyzer 20 to the PC main unit 26.

It can be seen that the gains of the coils 1 through 6 are maximum and free of noise when the frequency of the calibrating electric currents flowing through the planar coils 58$_k$ is in the range from 1.3 [MHz] to 1.5 [MHz]. This is because the resonant frequency of the planar coil $58_k$ (see FIG. 2) and the capacitor 60 and the resonant frequency of the planar coil 30 and the capacitor 37 are set to a value in the range from 1.3 [MHz] to 1.5 [MHz]. If the frequency of the calibrating electric currents is the same as the resonant frequency, then the reactance components contained in the calibrating coil device 50 and the coils 1 through 6, are eliminated by the resonance, resulting in a reduction in the impedance and an increase in the gain.

Figure 15:
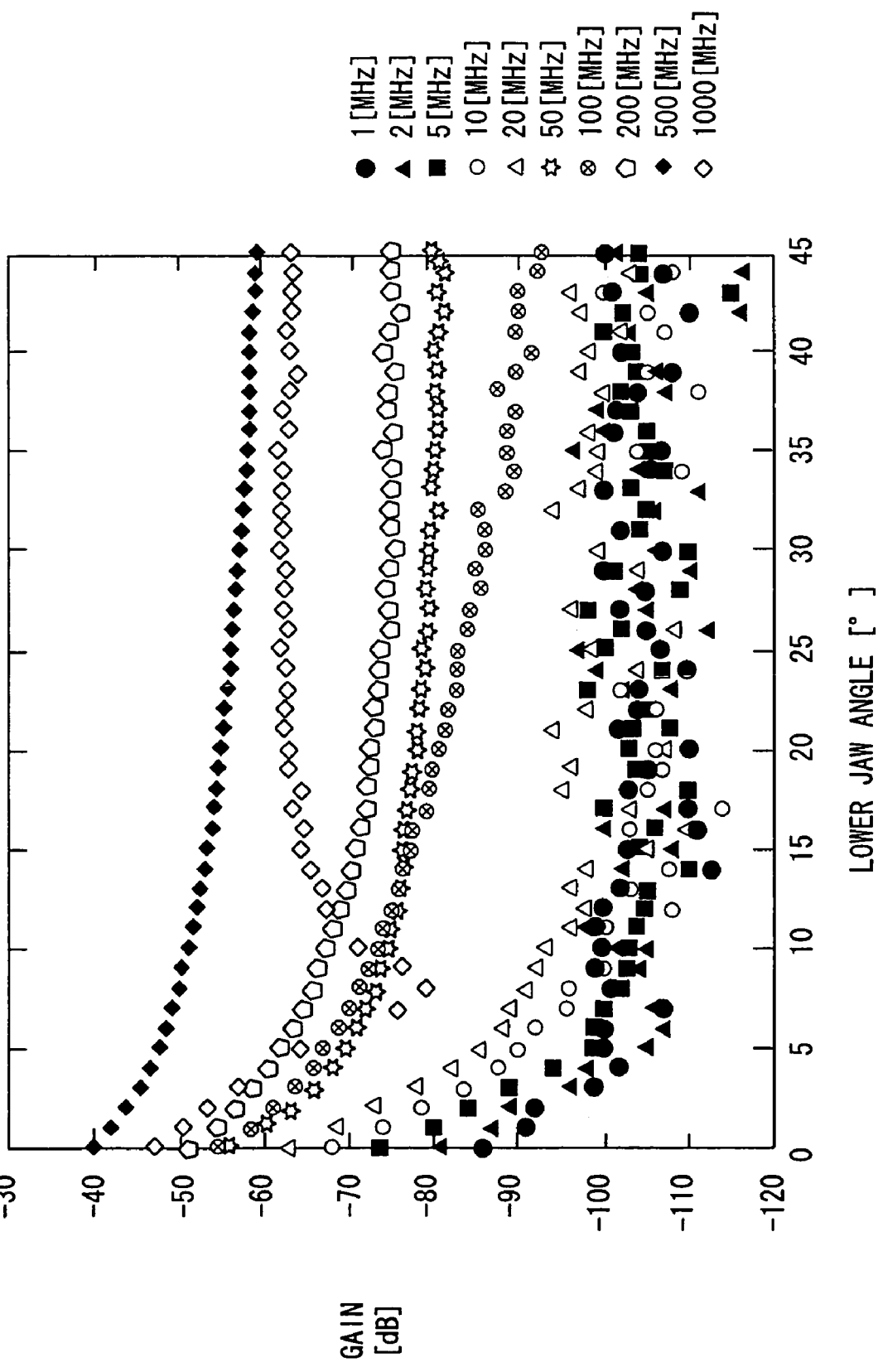
FIG. 15 is a characteristic diagram showing gain changes at the time the lower jaw is opened with respect to the upper jaw.

FIG. 15 shows gains between one magnetic generator $12_2$ and one magnetic field sensor $14_2$ at a time the lower jaw 24 is opened with respect to the upper jaw 22, the gains being plotted as the angle of the lower jaw 24 with respect to the upper jaw 22 is incremented successively by 1 [°].

In FIG. 15, while an alternating current flows through the planar coil 30 of the magnetic generator $12_2$, magnetic fluxes generated by the alternating current are detected by the planar coil 30 of the magnetic field sensor $14_2$. If the lower jaw 24 remains at the same angle, then the gain is greater as the frequency of the alternating current flowing through the planar coil 30 of the magnetic generator $12_2$ is higher. It can thus be seen that as the frequency of the alternating current is higher, the sensitivity of the magnetic field sensor $14_2$ is higher.

From the results shown in FIG. 15, if the accuracy of the network analyzer 20 is 0.1 [dB], for example, the distance by which the magnetic field sensor $14_2$ is moved when the lower jaw 24 is opened downwardly through 1 [°] with respect to the upper jaw 22, is 1.616 [mm], and a change caused in the gain when the lower jaw 24 is opened downwardly through 1 [°] is $\Delta S$ [dB], then the positional resolution of the magnetic field sensor $14_2$ is expressed according to the following equation (22):

$$\text{(Positional resolution)}=0.1\times1.616/\Delta S \text{ [mm]} \qquad (22)$$

Figure 16:
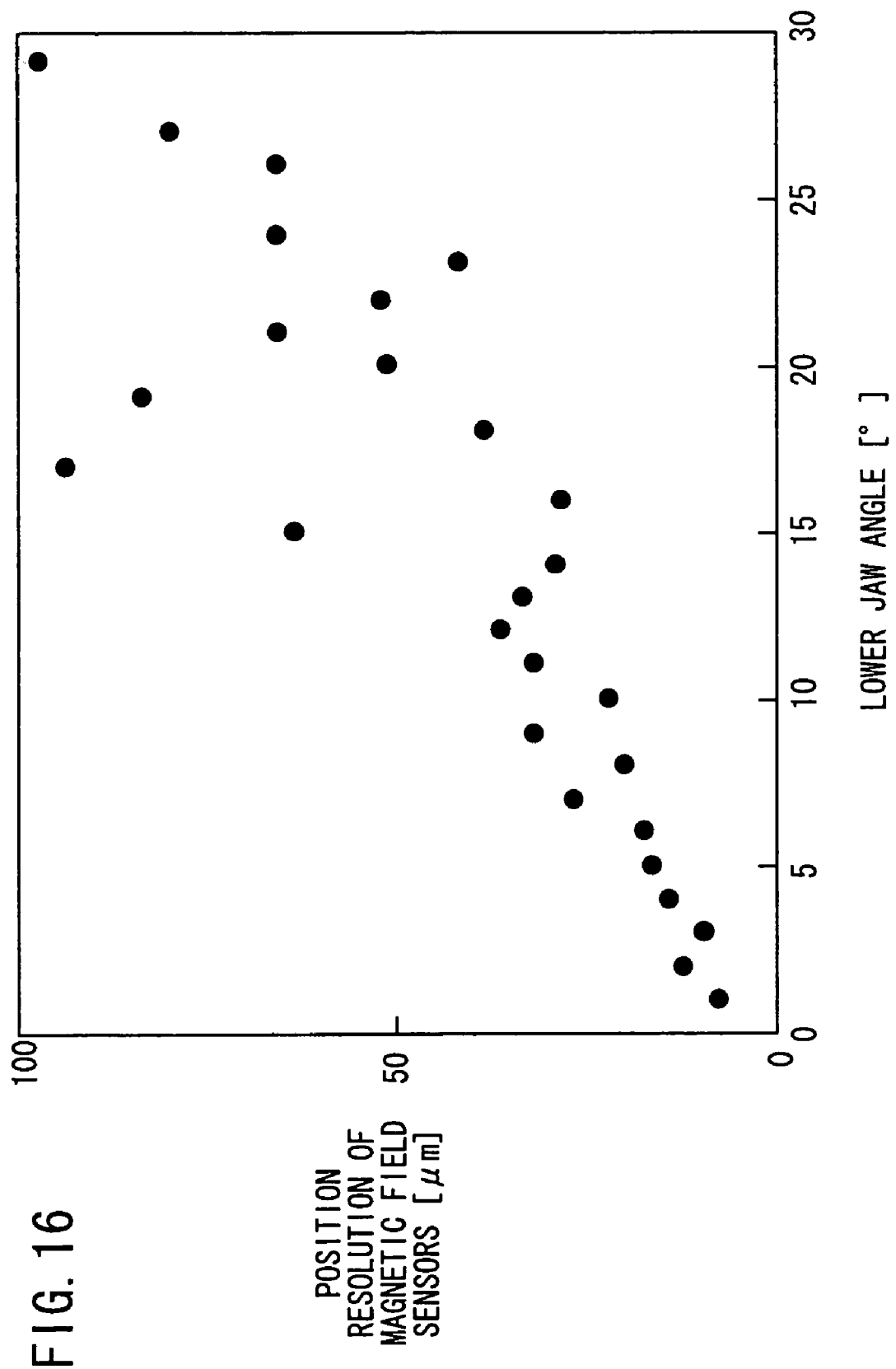
FIG. 16 is a characteristic diagram showing the positional resolution of the magnetic field sensors which is obtained from the measured results shown in FIG. 15.

FIG. 16 shows by way of example calculated results of the positional resolution of the magnetic field sensor $14_2$ which are determined by substituting the gains shown in FIG. 15 into the equation (22). In FIG. 16, the frequency of the calibrating alternating current flowing through the planar coil 30 of the magnetic generator $12_2$ is 500 [MHz].

It can easily be understood from the calculated results that if the angle through which the lower jaw 24 is opened, is in the range from 0 to 30 [°], then the positional resolution of the magnetic field sensor $14_2$ has a highest value of 8 [µm] and a lowest value of about 100 [µm], thereby achieving a positional accuracy within 100 [µm] in the three-dimensional jaw movement measuring apparatus 10.

According to the present embodiment, as described above, a plurality of magnetic generators $12_i$ are mounted on one of the upper jaw 22 and the lower jaw 24 and a plurality of magnetic field sensors $14_j$ are mounted on the other. One of the magnetic generators $12_i$ generates a measuring magnetic field, and one of the magnetic field sensors $14_j$ detects a flux density due to the measuring magnetic field. When the measuring magnetic field is generated, an electromagnetic coupling occurs between one of the magnetic generators $12_i$ and one of the magnetic field sensors $14_j$, and the magnetic field sensor $14_j$ converts the flux density into an electric signal (output current) by way of electromagnetic induction.

If there are at least six electromagnetic coupling combinations between the magnetic generators $12_i$ and the magnetic field sensors $14_j$, then parameters of six-degree-of-freedom movement with respect to the magnetic generators $12_i$ can be determined from the six detected measuring magnetic fields or electric signals, and the relative movement between the upper jaw 22 and the lower jaw 24 can be calculated from the parameters.

According to the present embodiment, therefore, the relative movement between the upper jaw 22 and the lower jaw 24 can be measured by providing six or more electromagnetic coupling combinations irrespectively of the mounted positions and mounted directions of the magnetic generators $12_i$ and the magnetic field sensors $14_j$. Therefore, the positional accuracy of the magnetic generators $12_i$ and the magnetic field sensors $14_j$ and the measuring accuracy of the magnetic field sensors $14_j$ are not lowered due to the mounted positions and mounted directions of the magnetic generators $12_i$ and the magnetic field sensors $14_j$.

Figure 17:
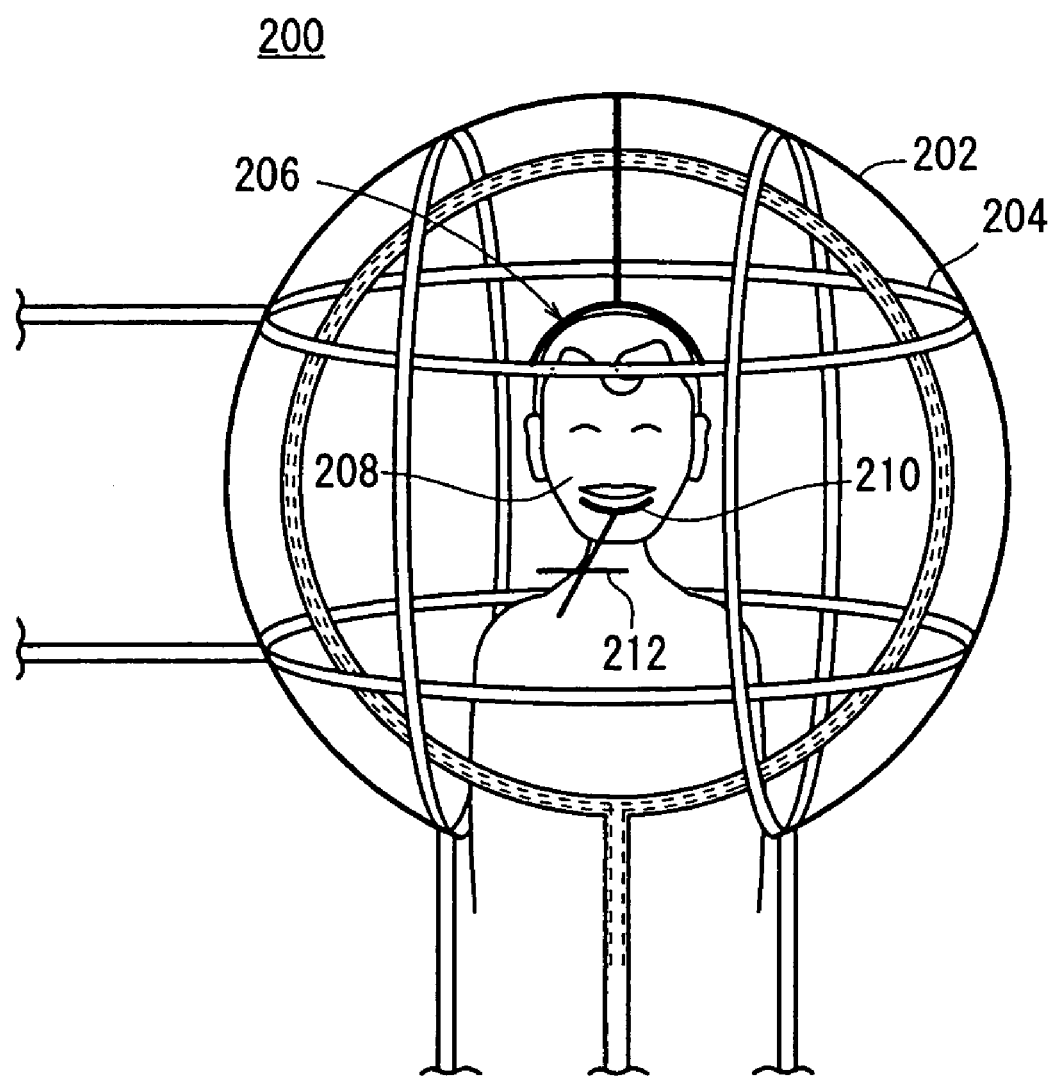
FIG. 17 is a view showing a conventional jaw movement measuring apparatus.

Since the magnetic generators $12_i$ and the magnetic field sensors $14_j$ are disposed between the upper jaw 22 and the lower jaw 24, the distance between the magnetic generators $12_i$ and the magnetic field sensors $14_j$ is smaller than with the conventional magnetic jaw movement measuring apparatus 200 (see FIG. 17), and the positional gradient of the magnetic field detected by each of the magnetic field sensors $14_j$ is greater. Therefore, the level of the electric signal output from each of the magnetic field sensors $14_j$ is higher, and the measuring accuracy of each of the magnetic field sensors $14_j$ is higher.

Inasmuch as the magnetic generators $12_i$ and the magnetic field sensors $14_j$ are mounted directly on the surfaces of the tooth crowns of upper jaw teeth on the upper jaw 22 and surfaces of the tooth crowns of lower jaw teeth on the lower jaw 24, when the upper jaw 22 and the lower jaw 24 are moved relatively to each other, the magnetic generators $12_i$ and the magnetic field sensors $14_j$ also move in unison with the upper jaw 22 and the lower jaw 24, respectively.

Therefore, even though the upper jaw 22 and the lower jaw 24 are moved relatively to each other, the magnetic generators $12_i$ and the magnetic field sensors $14_j$ are not positionally shifted from their original positions. Consequently, the measuring accuracy of the magnetic field sensors $14_j$ and the positional accuracy of the magnetic generators $12_i$ and the magnetic field sensors $14_j$ can be increased.

Inasmuch as the magnetic generators $12_i$ and the magnetic field sensors $14_j$ are disposed directly on the upper jaw 22 and the lower jaw 24, it is easy to reduce the size of the three-dimensional jaw movement measuring apparatus 10.

If the total number of the magnetic generators $12_i$ and the magnetic field sensors $14_j$ is increased to six or more, then the positional accuracy of the magnetic generators $12_i$ and the magnetic field sensors $14_j$ can further be increased.

The coils of the magnetic generators $12_i$ and the magnetic field sensors $14_j$ are in the form of planar coils. Therefore, the planar coils 30 can easily be mounted on the upper jaw 22 and the lower jaw 24, and when the upper jaw 22 and the lower jaw 24 are moved relatively to each other, any positional shift of the magnetic generators $12_i$ and the magnetic field sensors $14_j$ from their original positions is further reduced. Since the planar coils 30 can be fabricated by printing or the like, they can be produced more accurately and less costly than biaxial or triaxial coils.

According to the present embodiment, an alternating current flows through each of the magnetic generators $12_i$ to generate an alternating magnetic field from the planar coil 30. Since the electric signal output from each of the magnetic field sensors $14_j$ is proportional to the frequency of the alternating magnetic field, each of the magnetic field sensors $14_j$ outputs an electric signal having a higher level as the frequency of the alternating magnetic field is higher. Therefore, the positional resolution of the magnetic generators $12_i$ and the magnetic field sensors $14_j$ with respect to positional detection can be increased.

If the frequency of the alternating magnetic field is increased, then it is possible to eliminate low-frequency noise such as noise due to commercial frequencies, noise due to a changing magnetic field of the geomagnetism, and noise due to moving vehicles. Consequently, the three-dimensional jaw movement measuring apparatus 10 is made resistant to low-frequency noise.

If the capacitors 37, 60 are connected in parallel to or in series to the planar coils 30, $58_k$, and the planar coils 30, $58_k$ generate alternating magnetic fields having the resonant frequency of the planar coils 30, $58_k$ and the capacitors 37, 60, then reactance components in the calibrating coil device 50 and the magnetic generators $12_i$ can be removed by the resonance between the planar coils 30, $58_k$ and the capacitors 37, 60, thereby making it possible to further increase the level of the electric signal output from each of the magnetic field sensors $14_j$. Therefore, the positional resolution of the magnetic generators $12_i$ and the magnetic field sensors $14_j$ can be further increased.

Since the coils of the calibrating coil device 50 are in the form of planar coils $58_k$, when the planar coils $58_k$ are directly mounted on the upper jaw 22 or the lower jaw 24, the planar coils $58_k$ can more reliably be fixed to the upper jaw 22 or the lower jaw 24. Therefore, the positional accuracy of the magnetic generators $12_i$ and the magnetic field sensors $14_j$ can be further increased. Further, the planar coils $58_k$ can be placed so as not to obstruct natural jaw movement.

According to the present embodiment, the magnetic generators $12_i$ and the magnetic field sensors $14_j$ are mounted in small, optically concealed locations in the oral cavity or the like of the examinee 16, the coils of the magnetic generators $12_i$ and the magnetic field sensors $14_j$ are in the form of planar coils 30, and the coaxial cables 38 connected to these planar coils 30 comprise coaxial cables of small diameter. Since each of the magnetic generators $12_i$ functions as a marker coil, the positions and directions of each of magnetic generators $12_i$ and the magnetic field sensors $14_j$ can be measured by the three-dimensional jaw movement measuring apparatus 10 when the examinee 16 makes a jaw movement. Therefore, the three-dimensional jaw movement measuring apparatus 10 can be used for patients with temporomandibular disorder, who need to be accurately checked for jaw movement in dental examination, for measuring jaw movement with higher accuracy and reliability.

Since only the magnetic generators $12_i$, the magnetic field sensors $14_j$, and the coaxial cables 38 are inserted in the oral cavity of the examinee 16, the burden on the examinee 16 is reduced, and particularly the burden on children and aged people is greatly reduced. Thus, six-degree-of-freedom jaw movement can be measured with a positional accuracy of 100 [μm] or less, for example.

Since both the magnetic generators $12_i$ and the magnetic field sensors $14_j$ are inserted in the oral cavity of the examinee 16, the three-dimensional jaw movement measuring apparatus 10 can be reduced in size and cost. The three-dimensional jaw movement measuring apparatus 10 can therefore easily be introduced into dental clinics, for example, for raising the general standard of dentistry medical treatment.

Further, if each of the magnetic generators $12_i$, magnetic field sensors $14_j$ and coaxial cables 38 is changed for every measuring of a patient's jaw movement, it is possible to provide more hygienic three-dimensional jaw movement measuring apparatus 10.

The apparatus for and the method of measuring three-dimensional movement according to the present invention are not limited to the above embodiment, but may take any of various forms without departing from the gist of the present invention.

INDUSTRIAL APPLICABILITY

With the apparatus for and the method of measuring three-dimensional movement according to the present invention, since there are six or more electromagnetic coupling combinations of magnetic generators and magnetic field sensors, the parameters of six-degree-of freedom movement with respect to each of the magnetic generators can be determined from six detected measuring magnetic fields or electric signals, and a relative movement of at least two objects can be calculated from the parameters. Therefore, the relative movement of the two objects can be measured irrespectively of the mounted positions and mounted directions of the magnetic generators and the magnetic field sensors. A reduction in the positional accuracy of the magnetic generators and the magnetic field sensors and a reduction in the measuring accuracy of the magnetic field sensors due to the manner in which the magnetic generators and the magnetic field sensors are mounted in place, can advantageously be suppressed.

Since the magnetic generators are mounted on one of the objects and the magnetic field sensors on the other object, the distance between the magnetic generators and the magnetic field sensors is smaller than with the conventional three-dimensional magnetic jaw movement measuring apparatus, and the positional gradient of the magnetic field detected by each of the magnetic field sensors is greater. Therefore, the level of the electric signal output from each of the magnetic field sensors is higher, and the measuring accuracy of each of the magnetic field sensors is higher.

Furthermore, because the magnetic generators and the magnetic field sensors are mounted directly on the two objects, the size of the three-dimensional jaw movement measuring apparatus can easily be reduced.

The invention claimed is:

1. An apparatus for measuring three-dimensional movement, comprising:
   a plurality of magnetic generators mounted on one of at least two relatively movable objects;
   a plurality of magnetic field sensors mounted on another object, for detecting magnetic fields of said magnetic generators out of contact therewith;
   signal processing means for calculating relative positions and directions between said magnetic generators and said magnetic field sensors from the magnetic fields detected by said magnetic field sensors; and
   a plurality of non-contact calibrating coils;
   wherein said magnetic generators and said magnetic field sensors are paired in at least five combinations;
   each of said calibrating coils is paired in a total of at least five combinations; and
   calibrating magnetic fields generated by said calibrating coils are detected by said magnetic generators and said magnetic field sensors to measure initial positions and initial directions of said magnetic generators and said magnetic field sensors.

2. An apparatus for measuring three-dimensional movement according to claim 1, wherein each of said magnetic generators and said magnetic field sensors is of a planar type, each of said magnetic generators generates a uniaxial magnetic field, and each of said magnetic field sensors detects the uniaxial magnetic field.

3. An apparatus for measuring three-dimensional movement according to claim 2, wherein each of said magnetic generators and said magnetic field sensors comprises a planar coil for generating and detecting said uniaxial magnetic field.

4. An apparatus for measuring three-dimensional movement according to claim 3, wherein a measuring magnetic field generated by each of said magnetic generators comprises an alternating magnetic field.

5. An apparatus for measuring three-dimensional movement according to claim 4, wherein each of said magnetic generators comprises said planar coil and a capacitor connected in parallel to or in series to said planar coil, and said measuring magnetic field generated by each of said magnetic generators comprises an alternating magnetic field having the resonant frequency of said planar coil and said capacitor.

6. An apparatus for measuring three-dimensional movement according to claim 1, wherein each of said calibrating coils comprises a uniaxial, biaxial, or triaxial coil.

7. An apparatus for measuring three-dimensional movement according to claim 1, further comprising:
- electromagnetic coupling switching means for switching electromagnetic coupling combinations between said magnetic generators and said magnetic field sensors and switching electromagnetic coupling combinations between said calibrating coils and said magnetic generators or said magnetic field sensors; and
- coaxial cables electrically connecting said magnetic generators, said magnetic field sensors, and said calibrating coils to said electromagnetic coupling switching means.

8. A method of measuring three-dimensional relative movement of at least two objects, comprising the steps of:
- mounting a plurality of magnetic generators on one of said two objects, mounting a plurality of magnetic field sensors on another object, with said magnetic generators and said magnetic field sensors being paired in at least five combinations;
- placing a plurality of calibrating coils near said magnetic generators and said magnetic field sensors out of contact therewith, and detecting calibrating magnetic fields generated by said calibrating coils with said magnetic generators and said magnetic field sensors to measure initial positions and initial directions of said magnetic generators and said magnetic field sensors when said two objects are not moving relatively to each other;
- removing said calibrating coils, and thereafter detecting a measuring magnetic field generated by one of said magnetic generators with one of said magnetic field sensors while electromagnetic coupling combinations between said magnetic generators and said magnetic field sensors are being switched by electromagnetic coupling switching means; and
- determining relative positions and directions of said magnetic generators with respect to said magnetic field sensors from magnetic fields detected by said magnetic field sensors, and calculating relative movement between said two objects.

9. An apparatus for measuring three-dimensional movement according to claim 1, wherein said two objects comprise two parts which move relatively to each other in a living body.

10. An apparatus for measuring three-dimensional movement according to claim 9 wherein said two objects on which said magnetic generators and said magnetic field sensors are mounted, comprise a combination of at least two of a part movable in unison with an upper jaw, a part movable in unison with a lower jaw, a tongue, and an artificial tooth mounted in an oral cavity.

11. An apparatus for measuring three-dimensional movement according to claim 9, wherein said magnetic generators and said magnetic field sensors are mounted in an oral cavity of an examinee.

12. A method of measuring three-dimensional relative movement according to claim 8, wherein said two objects comprise two parts which move relatively to each other in a living body.

13. A method of measuring three-dimensional relative movement according to claim 12, wherein said two objects comprise a combination of at least two of a part movable in unison with an upper jaw, a part movable in unison with a lower jaw, a tongue, and an artificial tooth mounted in an oral cavity.

14. A method of measuring three-dimensional relative movement according to claim 12, wherein said magnetic generators and said magnetic field sensors are monted in an oral cavity of an examinee.

* * * * *